(12) United States Patent
Halverson et al.

(10) Patent No.: US 9,880,102 B2
(45) Date of Patent: Jan. 30, 2018

(54) MICROWELL ARRAY ARTICLES AND METHODS OF USE

(71) Applicant: 3M INNOVATIVE PROPERTIES COMPANY, St. Paul, MN (US)

(72) Inventors: Kurt J. Halverson, Lake Elmo, MN (US); Raymond J. Kenney, Woodbury, MN (US); Olester Benson, Jr., Woodbury, MN (US); Raymond P. Johnston, Lake Elmo, MN (US); Guoping Mao, Woodbury, MN (US); Patrick R. Fleming, Lake Elmo, MN (US); George Van Dyke Tiers, St. Paul, MN (US); Naiyong Jing, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/671,422

(22) Filed: Aug. 8, 2017

(65) Prior Publication Data
US 2017/0363545 A1    Dec. 21, 2017

Related U.S. Application Data

(60) Continuation of application No. 14/877,411, filed on Oct. 7, 2015, now Pat. No. 9,759,663, which is a
(Continued)

(51) Int. Cl.
*G01N 21/64* (2006.01)
*G01N 21/75* (2006.01)
(Continued)

(52) U.S. Cl.
CPC .......... *G01N 21/75* (2013.01); *B01L 3/50853* (2013.01); *B29C 59/046* (2013.01); *G01N 21/03* (2013.01); *G01N 21/253* (2013.01); *G01N 21/31* (2013.01); *G01N 21/55* (2013.01); *G01N 21/6428* (2013.01); *G01N 21/6452* (2013.01);
(Continued)

(58) Field of Classification Search
None
See application file for complete search history.

(56) References Cited

U.S. PATENT DOCUMENTS

| | | |
|---|---|---|
| 2,128,307 A | 8/1938 | Lord et al. |
| 3,528,972 A | 9/1970 | Kalopissis et al. |

(Continued)

FOREIGN PATENT DOCUMENTS

| | | |
|---|---|---|
| DE | 26 54 952 | 6/1977 |
| EP | 1 262 764 | 12/2002 |

(Continued)

OTHER PUBLICATIONS

Ichikawa, M. et al.; Kogyo Kagaku Zasshi (1964) vol. 67(1) pp. 138-142.
(Continued)

*Primary Examiner* — Rebecca L Martinez
(74) *Attorney, Agent, or Firm* — Qiang Han; Michael G. Williams

(57) ABSTRACT

The disclosure provides microstructured articles and methods useful for detecting an analyte in a sample. The articles include microwell arrays. The articles can be used with an optical system component in methods to detect or characterize an analyte.

30 Claims, 10 Drawing Sheets

Related U.S. Application Data division of application No. 13/510,191, filed as application No. PCT/US2010/057621 on Nov. 22, 2010, now abandoned.

(60) Provisional application No. 61/263,640, filed on Nov. 23, 2009.

(51) Int. Cl.

| | | |
|---|---|---|
| *B01L 3/00* | (2006.01) | |
| *B29C 59/04* | (2006.01) | |
| *G01N 21/03* | (2006.01) | |
| *G01N 21/25* | (2006.01) | |
| *G01N 21/31* | (2006.01) | |
| *G01N 21/55* | (2014.01) | |
| *B29C 35/08* | (2006.01) | |
| *B29C 59/08* | (2006.01) | |
| *B29C 59/10* | (2006.01) | |
| *B29C 59/14* | (2006.01) | |
| *B29C 59/16* | (2006.01) | |
| *B29C 59/02* | (2006.01) | |

(52) U.S. Cl.
CPC ... *B01L 2200/0689* (2013.01); *B01L 2200/12* (2013.01); *B01L 2300/044* (2013.01); *B01L 2300/0654* (2013.01); *B01L 2300/0819* (2013.01); *B01L 2300/0822* (2013.01); *B01L 2300/0851* (2013.01); *B01L 2300/0887* (2013.01); *B29C 35/0888* (2013.01); *B29C 59/08* (2013.01); *B29C 59/10* (2013.01); *B29C 59/14* (2013.01); *B29C 59/16* (2013.01); *B29C 2035/0827* (2013.01); *B29C 2059/023* (2013.01); *G01N 2021/0346* (2013.01); *G01N 2201/0446* (2013.01); *G01N 2201/064* (2013.01); *G01N 2201/08* (2013.01)

(56) References Cited

U.S. PATENT DOCUMENTS

| | | | |
|---|---|---|---|
| 4,576,850 A | 3/1986 | Martens | |
| 5,175,030 A | 12/1992 | Lu et al. | |
| 5,183,597 A | 2/1993 | Lu | |
| 5,204,160 A | 4/1993 | Roouser | |
| 5,205,840 A | 4/1993 | Friswell et al. | |
| 5,384,571 A | 1/1995 | Myers et al. | |
| 5,691,846 A | 11/1997 | Benson, Jr. et al. | |
| 5,738,825 A | 4/1998 | Rudigier et al. | |
| 5,888,594 A | 3/1999 | David et al. | |
| 6,210,910 B1 | 4/2001 | Walt et al. | |
| 6,285,001 B1 | 9/2001 | Fleming et al. | |
| 6,395,124 B1 | 5/2002 | Oxman et al. | |
| 6,447,591 B1 | 9/2002 | Titterington et al. | |
| 6,692,611 B2 | 2/2004 | Oxman et al. | |
| 6,696,286 B1 | 2/2004 | Halverson et al. | |
| 6,778,336 B2 | 8/2004 | Tracy | |
| 6,824,820 B1 | 11/2004 | Kinning et al. | |
| 6,942,968 B1 | 9/2005 | Dickinson et al. | |
| 7,264,973 B2 | 9/2007 | Lin et al. | |
| 7,332,271 B2 | 2/2008 | O'Keefe et al. | |
| 7,396,579 B2 | 7/2008 | Owusu | |
| 7,632,682 B2 | 12/2009 | Hong et al. | |
| 8,039,270 B2 | 10/2011 | Dultz et al. | |
| 2003/0027327 A1 | 2/2003 | Cunningham et al. | |
| 2004/0086869 A1 | 5/2004 | Schembri | |
| 2005/0214174 A1 | 9/2005 | Pham et al. | |
| 2006/0228716 A1 | 10/2006 | Nobile et al. | |
| 2006/0228722 A1 | 10/2006 | Kim et al. | |
| 2007/0009883 A1 | 1/2007 | Coassin et al. | |
| 2007/0134784 A1 | 6/2007 | Halverson et al. | |
| 2007/0160811 A1 | 7/2007 | Gaides et al. | |
| 2007/0231541 A1 | 10/2007 | Humpal et al. | |
| 2008/0014630 A1 | 1/2008 | Furuki | |

FOREIGN PATENT DOCUMENTS

| | | |
|---|---|---|
| GB | 2 011 940 | 7/1979 |
| WO | WO 1995/11464 | 4/1995 |
| WO | WO 1999/65664 | 12/1999 |
| WO | WO 2003/016868 | 2/2003 |
| WO | WO 2004/024330 | 3/2004 |
| WO | WO 2008/008247 | 1/2008 |
| WO | WO 2009/033017 | 3/2009 |
| WO | WO 2009/033029 | 3/2009 |
| WO | WO 2011/063313 | 5/2011 |

OTHER PUBLICATIONS

Chem Abstr (1964) #11785.

Naiki, K.; "Studies on Disperse Dyes (XVI) Dyeability and Fastness of Aminoanthraquinones"; Sen'i Gakkaishi; vol. 15; 1959; pp. 203-208.

Rondelenz, Y. et al.; "Microfabricated arrays of femtoliter chambers allow single molecule enzymology" Nature Biotechnology, vol. 23, No. 3, 2005; pp. 361-365.

MICROWELL ARRAY ARTICLES AND METHODS OF USE

BACKGROUND

The ability to perform parallel microanalysis on minute quantities of sample is important to the advancement of chemistry, biology, drug discovery and medicine. Today, the traditional 1536-well microtiter plate has been surpassed by microwell arrays which have an even greater number of reaction chambers and use lesser amounts of reagents due to efforts focused on maximizing time, throughput, and cost efficiencies. Although there are several types of microwell arrays available, fabrication used to generate high fidelity microfeatures having dimensions in tens of microns such as wells are frequently slow and expensive. Examples of common fabrication methods to produce these microfeatures include soft lithography, lithography, preferential etching of pre-existing arrays, milling, diamond machining, laser ablation, chaotropic etching and the like. However, all of these methods suffer from cost and capability limitations to varying degrees. Further, it is a special challenge to make articles with high density microfeatures that exhibit the desired optical features that are found in low-density microwell articles (e.g. 96-well plates). In addition, many microwell materials prove to be incompatible with the components of bioassays and chemical reactions and result in problems such as low sensitivity, high background signal, and lack of reproducibility. Thus, there continues to be a need for the development of improved microwell arrays.

Certain fiber optic bundles have been used to create microwell arrays. To act as an efficient waveguide, each fiber element must consist of a high refractive index core surrounded by a low refractive index cladding. Selective removal of the core glass by chemical etching to create a microwell lowers the refractive index mismatch when the original glass is replaced with a lower refractive index aqueous solution typically used in biological assays. This diminishes the waveguide characteristics of the fiber leading to increased light penetration through the cladding material. To overcome this problem light absorbing materials, for example certain metals, have been deposited as a thin layer on the interior sidewalls of the etched microwells. In addition to optical limitations, the fiber optic materials are often incompatible with many reaction conditions, particularly assays which are conducted in aqueous solutions and contain sensitive enzymatic reagents. Two major sources of incompatibility are the dissolution of the fiber optic substrate into the solution contained in the reaction chamber and the chemical reaction of the fiber optic substrate with assay components (e.g., proteins, nucleic acids) contained in the chamber. These chemical effects are exacerbated by the high surface to volume ratio in each microwell. These effects tend to degrade the performance of assays and reactions conducted in the fiber optic reaction chambers and frequently require additional processing to render the devices compatible with biological assays.

Due to technical difficulties in currently used processes for fabricating and/or coating arrays meeting these optical and chemical requirements, the range of assays that can be conducted in microwell arrays remains limited. Accordingly, there is a need for cost effective, high density microwell arrays that are compatible with a variety of assay and/or reaction conditions.

SUMMARY

This disclosure relates to flexible microwell arrays comprising a flexible microstructured layer with an optically transmissive flexible layer coupled thereto.

In one aspect, the present disclosure provides an article. The article can comprise a microstructured layer with upper and lower major surfaces. The microstructured layer can comprise a plurality of optically-isolated microwells extending between the upper and lower major surfaces. The article further can comprise an optically-transmissive flexible layer coupled to the lower major surface of the microstructured layer. Each microwell in the microstructured layer can comprise a top opening, a bottom opening, and at least one side wall extending between the top opening and bottom opening. The optically-transmissive flexible layer can have a thickness of about 2 μm to about 50 μm.

In another aspect, the present disclosure provides an article. The article can comprise a microstructured layer with upper and lower major surfaces. The microstructured layer can comprise a plurality of optically-isolated microwells extending below the upper major surface. The article further can comprise an optically-transmissive flexible layer coupled to the lower major surface of the microstructured layer. Each microwell in the microstructured layer can comprise an opening, an optically-transmissive bottom wall, and at least one side wall extending between the opening and the bottom wall. The bottom wall can have a thickness of about 0.1 μm to about 5 μm.

In another aspect, the present disclosure provides an article. The article can comprise a microstructured layer with upper and lower major surfaces. The microstructured layer can comprise a plurality of optically-isolated microwells extending below the upper major surface. The article further can comprise an optically-transmissive flexible layer coupled to the lower major surface of the microstructured layer. Each microwell in the microstructured layer can comprise an opening, an optically-transmissive bottom wall, and at least one side wall extending between the opening and the bottom wall. A thickness (t) can be defined by a thickness of the bottom wall plus a thickness of the optically-transmissive flexible layer. Thickness (t) can be about 2 μm to about 55 μm.

In any of the above embodiments, the microstructured layer can comprise a colorant. In any of the above embodiments, the colorant can be selected from the group consisting of carbon black, fuchsin, carbazole violet, and Foron Brilliant Blue.

In any of the above embodiments, the optically-transmissive flexible layer can be transmissive to a selected wavelength of light. In any of the above embodiments, the bottom wall can be substantially transmissive to the selected wavelength of light. In some embodiments, the at least one sidewall can be substantially nontransmissive to the selected wavelength of light. In some embodiments, the at least one sidewall can be at least 50% less transmissive of a selected wavelength of light than the bottom wall. In some embodiments, the at least one sidewall can be at least 90% less transmissive of a selected wavelength of light than the bottom wall.

In any of the above embodiments, the bottom wall and/or the at least one side wall of a microwell further can comprise a coating. In some embodiments, the bottom wall and/or the at least one side wall of a microwell further comprise a plurality of coatings. In any of the above embodiments, the coating can comprise $SiO_2$. In any of the above embodiments, the coating can comprise a reflective coating.

In any of the above embodiments, microstructured layer can comprise a cured polymer derived from a resin. In some embodiments, the resin can be selected from the group consisting of acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof.

In any of the above embodiments, the optically-transmissive layer can comprise a film. In some embodiments, the film can comprise polyethylene terephthalate, polyethylene naphthalate, high density polyethylene, low density polyethylene, or linear low density polyethylene. In any of the above embodiments, the film can comprise a multilayer film. In any one of the above embodiments, the optically-transmissive layer further can comprise an adhesive.

In any of the above embodiments, the microstructured layer further can comprise a region that is substantially free of microwells. In some embodiments, the region can comprise a detachable portion.

In any of the above embodiments, the article further can comprise a cover layer coupled to the upper major surface of the microstructured layer. In any one of the above embodiments, the article further can comprise a cover layer coupled to the optically-transmissive flexible layer on a surface opposite the microstructured layer. In any of the above embodiments, the cover layer may be removably coupled.

In any of the above embodiments, the article further can comprise an optical detection system comprising an optical device optically coupled to the article. In some embodiments, the optical device can be optically coupled to the microstructured layer. In some embodiments, the optical device can be optically coupled to the optically-transmissive flexible layer. In some embodiments, the coupling can comprise a fiber optic face plate. In some embodiments, the optical device can comprise a CCD image sensor, a CMOS image sensor, or a photomultiplier tube. In some embodiments, the optical system further can comprise a processor.

In any of the above embodiments, at least one microwell further can comprise a polynucleotide. In any of the above embodiments, at least one microwell can comprise a polypeptide. In any of the above embodiments, at least one microwell can comprise a particle. In some embodiments, a polynucleotide or a polypeptide can be coupled to the particle.

In another aspect, the present disclosure provides a process for manufacturing a microwell array article. The process can comprise providing a tool having a molding surface with a plurality of projections extending therefrom suitable for forming the microstructure elements; a flowable resin composition; and an optically-transmissive flexible layer having first and second major surfaces. The first major surface of the optically-transmissive flexible layer can be surface-treated to promote adhesion to a cured resin composition. The thickness of the optically-transmissive flexible layer can be about 50 µm or less. The process further can comprise applying to the molding surface a volume of the resin composition suitable for forming microstructure elements. The process further can comprise contacting the resin composition with a first major surface of the optically-transmissive flexible layer. The process further can comprise curing the resin while it is in contact with the flexible layer to form a microwell array article comprising a microstructured layer including a microwell array bonded to the flexible layer. The process further can comprise removing the microwell array article from the tool.

In any of the above embodiments of the process, contacting the resin composition with the first major surface of the optically-transmissive flexible layer can comprise applying pressure to the resin composition to substantially displace the resin between the tops of the projections in the tool and the surface of the optically-transmissive layer. In any of the above embodiments of the process, the flexible layer can be surface-treated to promote adhesion to the cured resin composition. Surface treatments can be selected from the group consisting of radiation treatments, corona discharge treatment, flame treatment, plasma treatment, high energy UV treatment, and chemical priming treatment. In any of the above embodiments of the process, the flexible layer can be coupled to a carrier. In any of the above embodiments of the process, the resin composition can comprise a colorant. In any of the above process embodiments, curing the resin composition can comprise exposing the resin composition to at least one curing treatment selected from the group consisting of actinic radiation from a radiation source, an electron beam, and a chemical curing agent. In any of the above embodiments of the process, the flexible layer can have a thickness of about 2 µm to about 48 µm. In any of the above embodiments, the process can further comprise the step of removing a portion of the microstructured layer. In any of the above embodiments, the process can further comprise the step of removing a portion of the optically-transmissive flexible layer. In any of the above embodiments, the process further can comprise disposing a reagent in a microwell. In any of the above embodiments of the process, the process further can comprise the step of coupling the microwell array article to a fiber optic device.

In another aspect, the present disclosure provides a method of detecting an analyte in a microarray. The method can comprise providing a sample suspected of containing an analyte, a reagent for the optical detection of the analyte, an optical detection system, and an article according to any of the above embodiments. The method further can comprise contacting the sample and the reagent in a plurality of microwells under conditions suitable to detect the analyte, if present, in a microwell. The method further can comprise using the optical system to detect the presence or absence of the analyte in a microwell.

In some embodiments of the method, the optical system can be optically coupled to the substrate. In some embodiments, the optical coupling can comprise a fiber optic face plate, wherein using the optical detection system can comprise passing a signal through the fiber optic face plate. In any of the above embodiments of the method, the optical system can comprise an optical device. In some embodiments, the optical device can comprise a CCD image sensor, a CMOS image sensor, or a photomultiplier tube. In any of the above embodiments of the method, the optical system further can comprise a processor.

In any of the above method embodiments, detecting the presence or absence of an analyte can comprise detecting light that is indicative of the presence of the analyte. In any of the above method embodiments, detecting light can comprise detecting light by absorbance, reflectance, or fluorescence. In any of the above method embodiments, detecting light can comprise detecting light from a lumigenic reaction.

In any of the above method embodiments, detecting the presence or absence of the analyte can comprise obtaining an image of a microwell. In some embodiments, detecting the presence or absence of the analyte can comprise displaying, analyzing, or printing the image of a microwell.

In any of the above method embodiments, contacting the sample and the reagent in a plurality of microwells under conditions suitable to detect the analyte can comprise contacting an enzyme and an enzyme substrate. In any of the above method embodiments, contacting the sample and the reagent in a plurality of microwells under conditions suitable to detect the analyte can comprise forming a hybrid between two polynucleotides.

In another aspect, the present disclosure provides an assay system. The system can comprise a microwell array article comprising an array of optically-isolated microwells and an imaging device coupled thereto. The array density can be ten or more microwells per square millimeter. In some embodiments, optically coupled can comprise adhesively coupling the microwell array article to a solid interface.

In another aspect, the present disclosure provides a composition. The composition can comprise a compound selected from the group consisting of 1-(3-methyl-n-butylamino)-9,10-anthracenedione; 1-(3-methyl-2-butylamino)-9,10-anthracenedione; 1-(2-heptylamino)-9,10-anthracenedione; 1,1,3,3-tetramethylbutyl-9,10-anthracenedione; 1,10-decamethylene-bis-(-1-amino-9,10-anthracenedione); 1,1-dimethylethylamino-9,10-anthracenedione; and 1-(n-butoxypropylamino)-9,10-anthracenedione. In some embodiments, the composition further can comprise a cured polymer. In any of the above embodiments, the cured polymer can be is derived from a resin selected from the group consisting of acrylate resins, acrylic resins, acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a substrate comprising "an" array can be interpreted to mean that the substrate can include "one or more" arrays.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the disclosure is not intended to describe each disclosed embodiment or every implementation of the disclosed articles, processes, and methods. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

FIG. 6b is a graph of the pixel intensities from the image of the microwell array article of FIG. 6a.

DETAILED DESCRIPTION

Figure 1:
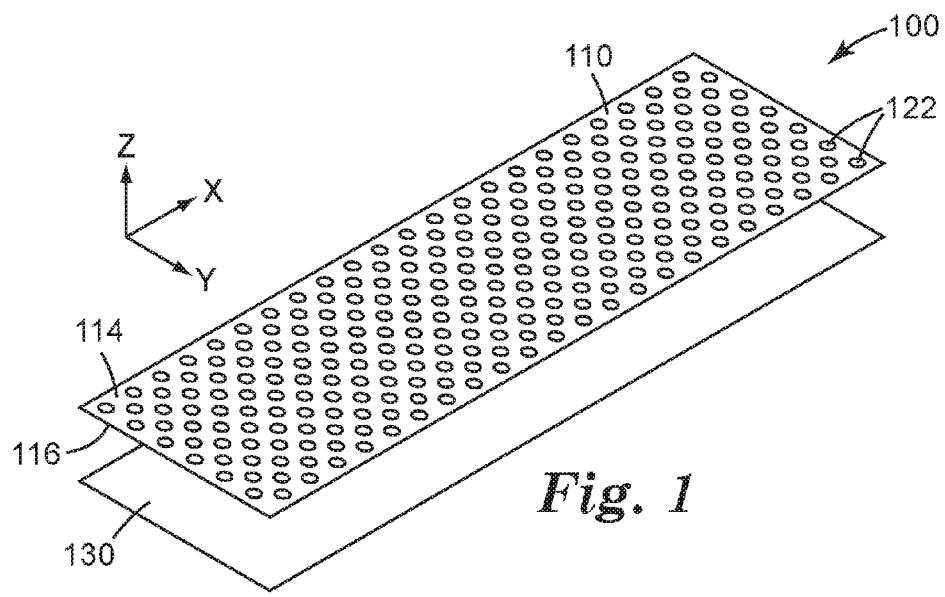
FIG. 1 is a top perspective exploded view, of one embodiment of a microwell array article according to the present disclosure.

The present disclosure provides array articles comprising a substrate containing individual reaction chambers (microwells). The disclosure includes the process of fabricating the array including methods of forming multilayered structures (e.g., laminates) comprising the substrate in which the array is formed, a flexible, optically-transmissive layer coupled thereto and, optionally, one or more removable protective layers. The inventors have discovered that it is particularly difficult to make flexible substrates with high-density microfeatures (e.g., reaction chambers) that are optically isolated in both axes of an X-Y plane, but remain optically transmissive in the corresponding Z axis. The inventors further have discovered that it is difficult to fabricate an array of optically-isolated microwells with a thin, flexible, highly-transmissive base. The present disclosure provides microwell arrays, and a process for making the microwell arrays, that overcome these difficulties. The inventive processes result in significant optical isolation of the individual reaction wells without the need for difficult, costly coating procedures to obtain the requisite optical isolation for extremely high-density microwell arrays.

The present disclosure further provides a system to detect an analyte. The detection system can comprise any of the array articles disclosed herein, wherein the array article is optically coupled to an optical device. The optical device may be an imaging device.

The disclosed articles can be used in an assay to detect an analyte. The assay can include the detection of a fluorescent or a luminescent signal emanating from a particular microwell in the array. The disclosed articles substantially prevent the transmission of selected wavelengths of light from one microwell to another through the sidewalls of the microwells. Simultaneously, the articles permit the transmission of substantial amounts of the selected wavelengths of light through the bottom wall of each microwell. Even further, the disclosed articles are configured to minimize the scatter of light emanating from the bottom of each microwell such that the light emanating from individual adjacent microwells in an array; in particular, a high-density array; can be resolved by a simple optical device.

Before any embodiments of the disclosure are explained in detail, it is to be understood that the disclosure is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the articles described herein will be used, mounted, displayed, or positioned in use.

The present disclosure is generally directed to methods and articles for detecting analytes in a sample. More particularly, the disclosure relates to microwell arrays that can be used to conduct multiple, independent assays simultaneously. The disclosed articles are adapted for use with a variety of optical systems to detect the presence or absence of an analyte in a sample.

Definitions

Unless otherwise defined, all technical and scientific terms used herein have the same meaning as commonly understood by one of ordinary skill in the relevant art to. Methods and materials similar or equivalent to those described herein can be used in the practice of the present disclosure, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents and other references are incorporated herein by reference in their entirety. In addition, the materials, methods, and examples are illustrative only and not intended to be limiting.

"Analyte" means a molecule, compound, composition or complex, either naturally occurring or synthesized, to be detected or measured in or separated from a sample of interest. Analytes include, without limitation, polypeptides (e.g., proteins), peptides, amino acids, fatty acids, nucleotides (e.g., ATP), polynucleotides (including, but not limited to DNA, RNA, cDNA, mRNA, PNA, LNA), carbohydrates, hormones, steroids, compounds, lipids, vitamins, bacteria, viruses, pharmaceuticals, and metabolites. An analyte may be one member of a ligand/anti-ligand pair or one member of a pair of polynucleotides having sufficient complementarity to participate in a hybridization event.

"Fiber optic faceplate" refers to a bundle of optical quality glass fibers which are fused together to form a monolithic structure which is then "sliced" and polished to form a "wafer" of required thickness.

"Functional groups" means any chemical or biological species capable of affixing a reactant or analyte to the inside surface of the reaction chamber.

"Impermeable to water" refers to the ability of a thin film to provide a barrier to an aqueous solution contained in the reaction chamber and to prevent leaching of the chamber solution into the wall components of the reaction chamber.

"Optically transparent" refers to the ability of light to transmit through a material. "Optically isolated", as used herein, refers to a condition whether by light that is directed into a microwell in an article or that is emitted by a component or a reaction contained in a microwell, is not substantially transmitted laterally through the article and detectably associated with a proximate microwell (i.e., less than 20% of the light; preferably, less than 10% of the light; more preferably, less than 5% of the light; even more preferably, less than 1% of the light is transmitted and detectably associated with a proximate microwell).

"Reactant" means any chemical or biological molecule, compound, composition or complex, either naturally occurring or synthesized, that is capable of binding, forming, or reacting with an analyte in a sample of interest either alone or in conjunction with another reactant. The reactants of the present disclosure are useful for chemical reaction or biochemical measurement, detection or separation. Examples of reactants include, without limitation, amino acids, nucleic acids, including oligonucleotides and cDNA, carbohydrates, and proteins such as enzymes and antibodies.

"Reaction Chamber" means a localized well or chamber (i.e. a hollowed-out space, having width and depth) on a substrate, comprising side walls and a bottom that is used to facilitate the interaction of reactants.

"Scanning Electron Microscopy" or "SEM" refers to a method for high resolution imaging.

"Substrate" refers to a solid support or any material that can be modified to contain discrete individual reaction chambers and is amenable to at least one detection method.

"Enzyme substrate" refers to a molecule that participates in an enzyme-catalyzed reaction.

"Thin film" refers to the coating of material deposited on the surface of the substrate less than 1 micron thick.

An "array of regions on a solid support" is a linear or two-dimensional array of preferably discrete regions, each having a finite area, formed on the surface of a solid support.

A "microwell array" is an array of reaction chambers having a density of discrete reaction chambers of at least about 100/cm$^2$, and preferably at least about 10/mm$^2$. The reaction chambers have a three-dimensional structure with dimensions, e.g., openings with, for example, diameters in the range of between about 5-250 μm, depths in the range between about 2 to 100 microns. By "array" herein is meant a plurality of reaction chambers, which are localized wells or chambers in an array format on the substrate material; the size of the array and its reaction chambers will depend on the composition and end use of the array.

The term "hybridization" refers to a process in which a single-stranded region of a nucleic acid molecule (DNA or RNA) is joined with a complementary single-stranded region of nucleic acid, again DNA or RNA, to form a double-stranded region. Hybridization includes intermolecular (between two distinct molecules) and intramolecular (between two regions of a single molecule) processes "Microspheres" or "beads" or "particles" or grammatical equivalents herein refer to small, discrete particles.

The term "probe" refers to poly peptide or a single-stranded nucleic acid molecule, with a known nucleotide sequence, which is labeled in some way (for example, radioactively, fluorescently, or immunologically) and used to selectively find and mark certain polypeptide, DNA, or RNA sequences of interest to a researcher by binding or hybridizing to it.

The term "cDNA" refers to DNA synthesized from an RNA template using reverse transcriptase.

The term "nucleotide" refers to a subunit of DNA or RNA consisting of a nitrogenous base (adenine, guanine, thymine, or cytosine in DNA; adenine, guanine, uracil, or cytosine in RNA), a phosphate molecule, and a sugar molecule (deoxyribose in DNA and ribose in RNA).

The term "oligonucleotide" refers to a compound comprising a nucleotide linked to phosphoric acid. When polymerized, it gives rise to a nucleic acid.

The term "biomolecule" refers to an organic molecule and especially a macromolecule (as a protein or nucleic acid) that may be found in and/or synthesized by a living organisms. The term "labeling" refers to attachment of a moiety to a macromolecule that enables it to be visualized or its presence detected using specific instrumentation.

The term "nucleic acid" refers to any of various acids (as an RNA or a DNA) composed of nucleotide chains.

The term "PNA (peptide nucleic acid)" refers to Peptide nucleic acid (PNA) monomers have a N-(2-aminoethyl) glycine backbone to which adenine, cytosine, guanine, or thymine bases are linked by amide bonds. Peptide nucleic acids are synthesized by creating an amide bond between an amino group of the backbone and a carboxyl group of another peptide nucleic acid monomer.

The term "non-specific binding (NSB)" refers to a phenomenon where a macromolecule interacts with a surface and is typically dependent on charge and/or hydrophobicity. In contrast, specific binding involves selective interactions between an antigen and its corresponding antibody, or complementary strands of nucleic acids.

The term "LNA (Locked Nucleic Acid)" consist of conformationally restricted oligonucleotide analogs. LNA is a bicyclic nucleic acid where a ribonucleoside is linked between the 2'-oxygen and 4'-carbon atoms with a methylene unit.

Analytes

The present disclosure provides articles and methods for detecting an "analyte" or a "target analyte". Biological assays include at least one biomolecule, which may take part in a biological assay as a binding partner (e.g., a receptor-ligand binding reaction, an antigen-antibody binding reaction, an enzyme-substrate binding reaction, a hybridization reaction between polynucleotide regions with at least partial homology). As will be appreciated by those in the art, a large number of analytes may be used in the present disclosure. For example, any target analyte can be used which binds a bioactive agent or for which a binding partner (e.g. a drug candidate) is sought.

Suitable analytes include organic and inorganic molecules, including biomolecules. When detection of a target analyte is performed, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including prokaryotic (such as pathogenic bacteria) and eukaryotic cells, including mammalian tumor cells); viruses (including retroviruses, herpes viruses, adenoviruses, lentiviruses, etc.); and spores; etc. Particularly preferred analytes are nucleic acids and proteins.

In a preferred embodiment, the target analyte is a protein. Protein detection in microwell array assays is described, for example, in U.S. Pat. No. 6,942,968; U.S. Patent Application Publication Nos. US 2003/0027327, US 2006/0228716, US 2006/0228722; and PCT International Publication No. WO 03/016868; each of which is incorporated herein by reference in its entirety. As will be appreciated by those in the art, there are a large number of possible proteinaceous target analytes that may be detected or evaluated for binding partners using the articles of the present disclosure. Suitable protein target analytes include, but are not limited to, (1) immunoglobulins; (2) enzymes (and other proteins); (3) hormones and cytokines (many of which serve as ligands for cellular receptors); and (4) other proteins.

Immunoglobulins include, but are not limited to, IgEs, IgGs and IgMs. Immunoglobulins include therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antiepileptic drugs (phenytoin, primidone, carbariezepin, ethosuximide, valproic acid, and phenobarbital), cardioactive drugs (digoxin, lidocaine, procainamide, and disopyramide), bronchodilators (theophylline), antibiotics (chloramphenicol, sulfonamides), antidepressants, immunosuppressants, abused drugs (amphetamine, methamphetamine, cannabinoids, cocaine and opiates) and antibodies to any number of viruses (including orthomyxoviruses, (e.g. influenza virus), paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus, enteroviruses (e.g. poliovirus, coxsackievirus), hepatitis viruses (including A, B and C), herpes viruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtherias; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like).

Enzymes (and other proteins) include, but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphatase; aldolase, prostatic acid phosphatase, terminal deoxynucleotidyl transferase, and bacterial and viral enzymes such as HIV protease.

Hormones and cytokines (many of which serve as ligands for cellular receptors) include, but are not limited to, erythropoietin (EPO), thrombopoietin (TPO), the interleukins (including IL-I through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progesterone, testosterone.

Nonlimiting examples of other proteins include α-fetoprotein and carcinoembryonic antigen (CEA).

In addition, any of the biomolecules for which antibodies may be detected may be detected directly as well; that is, detection of virus or bacterial cells, therapeutic and abused drugs, etc., may be done directly.

In a preferred embodiment, the target analyte is a nucleic acid. These assays find use in a wide variety of applications. In a preferred embodiment, probes may be used in genetic diagnosis. For example, probes can be made to detect target sequences such as the gene for nonpolyposis colon cancer, the $BRCA_1$ breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the articles of the disclosure. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-11, may be detected in this way. Bacterial infections such as tuberculosis, *chlamydia* and other sexually transmitted diseases, may also be detected.

Flexible Microwell Arrays

FIG. 1 shows a top perspective exploded view of one embodiment of an article 100 of the present disclosure. The article 100 comprises a microstructured layer 110 with an upper major surface 114 and a lower major surface 116. The upper major surface 114 comprises an array of optically-isolated microwells 122. The article 100 further comprises an optically-transmissive flexible layer 130 coupled to the lower major surface 116 of the substrate 110. FIG. 1 further shows a set of axes to illustrate that, preferably, the microwells 122 are optically isolated such that light is not substantially transmitted within the plane formed by the X-Y axes. However, light can be substantially transmitted from the microwells 122 in a direction that is predominantly oriented toward the Z axis or, preferably, substantially parallel with the Z axis.

Figure 4:
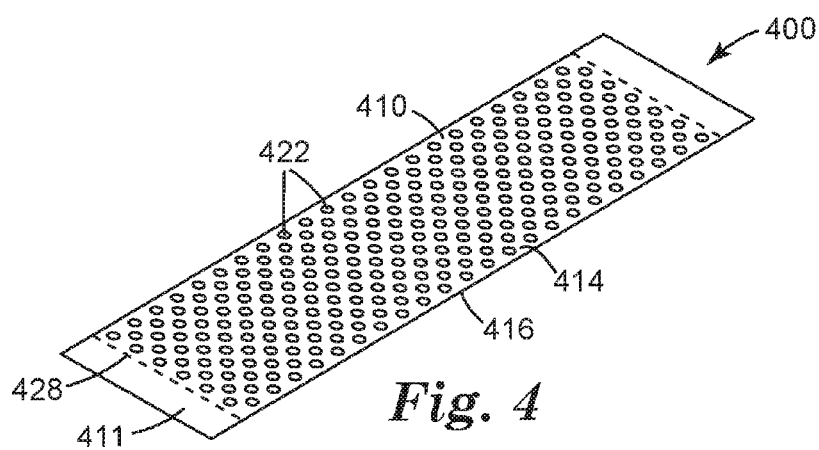
FIG. 4 is a top perspective view of an embodiment of a microwell array article comprising a tab portion according to the present disclosure.

FIG. 4 shows a top perspective view of another embodiment of an article 400 according to the present disclosure. In this embodiment, the article 400 comprises a microstructured layer 410 with an upper major surface 414 and a lower major surface 416. Microwells 422 extend below the upper major surface 414 of the microstructured layer 410. Also shown in FIG. 4 is a tab portion 411 of the microstructured layer 410. The tab portion 411 may be located in any position on the periphery of the microstructured layer 410 and can serve as a region at which the article 400 can be grasped and/or handled without contacting a microwell 422. The article may comprise a single tab region 411 or, preferably, a plurality of tab portions 411 (as shown) to provide multi-point control of the article 400 during handling. Optionally, the microstructured layer 410 may comprise perforations 428, or the like, such that the tab portion 411 may be detached from the article 400 during or after use.

The microwells or chambers in the microstructured layer each have at least one side wall, a bottom wall and both width and depth. Reaction mixtures, assay solutions, or microparticles can be deposited into each microwell. The microwells are preferably of sufficient dimension and order to allow for (i) the introduction of the necessary reactants into the wells, (ii) chemical reactions or bioassays to take place within the wells and (iii) inhibition of mixing of particulate reactants and/or analytes between wells. The microwell can be any shape. In one embodiment, the shape of the microwell is preferably frustoconical, but the microwell can be multi-sided so as to approximate a cylindrical or frustoconical shape. The microwell can have a smooth wall surface. In some embodiments, the microwell can have at least one irregular wall surface. The bottom wall of the microwells can be either planar or concave or convex.

In general, the microstructured layer permits optical detection of the contents of each microwell. In some embodiments, the microstructured layer does not appreciably fluoresce. The microstructured layer is preferably made of a material that facilitates detection of a chemical reaction event or assay result in each microwell. For example, in a typical nucleic acid sequencing reaction, binding of a dNTP to a sample nucleic acid to be sequenced can be monitored by detection of photons generated by enzyme reacting with phosphate moiety liberated in the sequencing reaction. Thus, having the base of the microwell and the optically-transmissive flexible substrate be substantially transparent or light conductive facilitates detection of the photons.

In some embodiments, the microwells can be optically interrogated through the opening of the microwells. In some embodiments, the microwells can be optically interrogated through the bottom wall of the microwells. In some embodiments, the microwells can be optically interrogated through the opening of the microwells and through the bottom wall of the microwells.

In some embodiments, the microstructured layer comprises a colorant that is substantially nontransmissive to selected wavelengths of light. The disclosed articles of the present disclosure provide for a microwell array article wherein selected wavelengths of light are substantially transmitted through the bottom wall of each microwell while the selected wavelengths of light are substantially absorbed by the side walls of each microwell, thereby reducing the incidence of optical cross-talk between adjacent microwells.

The microwells can be in a pattern, i.e. a regular design or configuration, or the microwells can be randomly distributed on the array surface. In one embodiment, there is a regular pattern of microwells such that the chambers may be addressed in the X-Y coordinate plane. "Pattern" in this sense includes a repeating unit, preferably one that allows a high density of microwells on the substrate.

The shape of the microwells in the microstructured layer can be selected to impart desirable effects on the signal production. That is, the wells can be square, round or polygonal (e.g., pentagonal, hexagonal, octagonal) in shape. Preferably, the side walls of the microwells are substantially straight and form an angle (with the substantially planar surface of the microwell array) that is greater than 90 degrees. The angled side wall produces a frustoconical-shaped microwell in an embodiment wherein the opening and the bottom wall of the microwell are circular in shape, for example.

The array pattern may comprise a composite array. As will be appreciated by one skilled in the art, a configuration of a composite array is not limited to the dimensions of a microtiter plate. A composite array configuration may be a single array, or may be a one-dimensional composite of arrays, i.e. a composite array having only one array in a first dimension and a plurality of arrays in a second dimension. Furthermore, a composite array can be a square, e.g., 2×2, 3×3, etc., or any other configuration, including, but not limited to, concentric circles, spiral, rectangular, triangular, and the like. Preferably, the composite of arrays contain regularly spaced arrays in lattice configuration. In certain embodiments, the composite of arrays forms a square or rectangular lattice.

In a preferred embodiment, the microwells are separated with spaces between each other. As is appreciated by those skilled in the relevant art, the spacing is determined by calculating the distance between centers. Varying the spacing between sites can result in the formation of arrays of high density, medium density or lower density. The microwells may be spaced any suitable distance apart. Spacing is determined by measuring the distance between the center points of two adjoining microwells. The microwells are generally spaced between 5 μm and 200 μm apart. In some embodiments, the microwells may be spaced about 10 μm to about 100 μm apart. In some embodiments, the microwells may be spaced about 12 μm to about 80 μm apart. In some embodiments, the microwells may be spaced about 15 to about 50 μm apart. A particular advantage of spacing wells apart is that commercial optical devices (e.g., cameras, scanners) can be used to analyze the arrays. The resolution of optical devices may vary and arrays can be formed that allow for detection on high or low resolution optical devices. In both cases, various software packages (e.g., GENEPIX software package by AXON instruments, ImagePro from Media Cybernetics, or others that are provided with conventional fluorescent microscope scanning equipment) are used to analyze the image from the optical device. In a preferred embodiment, the software employs contrast-based or other image processing algorithms to resolve the microwells and extract signal intensity information.

In some embodiments, a microparticle is disposed in at least one microwell of the microwell array. In some embodiments, a microparticle is disposed in at least 25% of the microwells of the microarray. In some embodiments, a microparticle is disposed in at least 50% of the microwells of the microwell array. In some embodiments, a microparticle is disposed in at least 75% of the microwells of the microwell array. In some embodiments, a microparticle is disposed in at least 90% of the microwells of the microwell array. In some embodiments, a microparticle is disposed in about 100% of the microwells of the microwell array.

The size of the microwell can be made to accommodate any volume. In some embodiments, the microwell volume is about 1 to about 1000 picoliters. In some embodiments, the microwell volume is about 5 to about 100 picoliters. In some embodiments, the microwell volume is about 20 to about 50 picoliters. In some embodiments, the microwell volume is about 25 picoliters.

The microwells may have any suitable width. In one embodiment, the microwells have a diameter (width) in one dimension of about 3 μm to about 100 μm. In one embodiment, the microwells have a diameter (width) in one dimension of about 5 μm to about 70 μm. In some embodiments, the microwells have a diameter (width) in one dimension of about 10 μm to about 50 μm.

The microwells may have any suitable depth. The depth of substantially all of the microwells is generally about 5 μm to about 100 μm. In some embodiments, the depth of substantially all of the microwells is about 10 μm to about 60 μm. In some embodiments, the depth of substantially all of the microwells is about 30-40 μm. Substantially all of the microwells means at least 90% of the microwells. In some embodiments, substantially all of the microwells means at least 95% of the microwells. In some embodiments, substantially all of the microwells means at least 97% of the microwells. In a further embodiment, substantially all of the microwells means at least 99%, more preferably all, of the microwells. The depth of a microwell can be measured, for example using a Wyko NT9100 Optical Profiler (Veeco, Plainview, N.Y.). Routine microwell depth measurements can be made using the area difference plot feature of the instrument. The instrument can compare the depth of a plurality of microwells to a reference point on a flat surface of the substrate to provide an average microwell depth.

The array preferably comprises a sufficient number of microwells to carry out such numerous individual assays. The array can contain any number of microwells. Depending on the end use of the array, substrates are made to comprise a certain number of microwells (e.g., greater than 20,000 microwells, greater than 100,000 microwells, greater than 1,000,000 microwells, greater than 5,000,000 microwells).

Figure 2A:
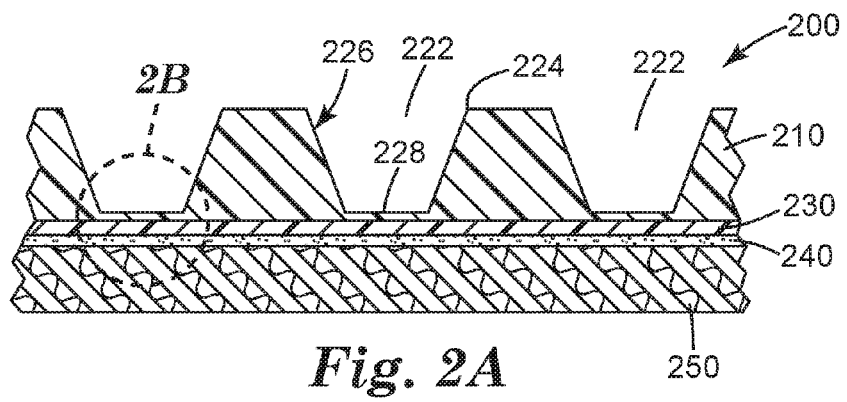
FIG. 2A is a cross-sectional view of one embodiment of a microwell array article.

FIG. 2A shows a cross-sectional view of one embodiment of a microwell array article 200 according to the present disclosure. The article 200 comprises a microstructured layer 210. The microstructured layer 210 comprises an array of optically isolated microwells 222. Each microwell 222 comprises an opening 224, a bottom wall 228, and at least one side wall 226 extending from the opening 224 to the bottom wall 228.

The microstructured layer 210 can be formed from a suitable material using a curing process described herein. Suitable materials include polymer materials (e.g., acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof) that can be processed to form a unitary, flexible microstructured layer 210 comprising a plurality of microwells 222, each microwell 222 with a bottom wall 228 that is, for example, about 0.2 μm to about 6 μm thick. In some embodiments, the polymer materials are substantially impermeable to water. In some embodiments, the substrate can be coated with one or more materials, as described herein.

The microstructured layer 210 is coupled to an optically-transmissive flexible layer 230. In some embodiments, the optically-transmissive flexible layer 230 substantially permits the transmission of visible wavelengths of light there through. In some embodiments, the optically-transmissive flexible layer 230 further permits the transmission of ultraviolet wavelengths of light there through. In some embodiments, the optically-transmissive flexible layer 230 comprises a polymeric material. Nonlimiting examples of suitable polymeric materials include polyethylene naphthalate (PEN), PET (polyethylene terephthalate, PEN (polyethylene naphthalate), HDPE (high density polyethylene, LDPE (low density polyethylene), LLDPE (linear low density polyethylene). PET and PEN are particularly preferred.

Optionally, the microwell array article 200 can comprise an adhesive layer 240. In some embodiments, the adhesive layer 240 can be incorporated into the microwell array article 200 by coating an adhesive onto the optically-transmissive flexible layer 230. In some embodiments, the adhesive layer 240 can be transferred to the microwell array article 200 by transferring the adhesive layer 240 from a carrier to the optically-transmissive flexible layer 230 via lamination processes that are known in the art, for example. Preferably, the adhesive layer 240 substantially permits the transmission of light (e.g., ultraviolet and/or visible wavelengths of light).

The optional adhesive layer 240 can couple the microwell array article 200 to a variety of substrates 250 that can serve at least one of a variety of functions. In some embodiments, substrate 250 can be a flexible carrier (e.g., paper, coated paper, polymeric film, metal film) that functions to carry the microstructured layer 210 or the materials that form the microstructured layer 210 during a processing step. In some embodiments, the substrate 250 can be a rigid or a flexible material (e.g., a glass slide, a plastic film, coated paper) and can function as a protective layer to retain functional properties (e.g., structure, shape, size, chemical integrity, optical properties, and/or adhesion properties) associated with the article. In some embodiments, the substrate 250 may be a component of a package to contain the microwell array article 200, as described herein and in U.S. Patent Application No. 61/236,612, filed Nov. 23, 2009 and entitled "CARRIER FOR FLEXIBLE MICROASSAY DEVICE AND METHODS OF USE", which is incorporated herein by reference in its entirety. In some embodiments, the substrate 250 may be a component of an imaging system (e.g., a camera, a lens, a fiber optic bundle).

The substrate 250 can be a flexible component that can be used for a variety of purposes. Nonlimiting examples of flexible substrates include polymer films, metal films, or paper. In some embodiments, the substrate 250 is a carrier (e.g., a release liner) that is coated with adhesive 240 in order to transfer the adhesive 240 to the optically-transmissive flexible layer 230. Preferably, in these and other embodiments, the substrate 250 is coated with a release chemistry such as a silicone, fluorosilicone, wax, or other low surface energy material to facilitate release of the adhesive layer 240 from the substrate 250. Flexible substrates can be used for processing, carrying, and/or protecting the microwell array articles from damage or contamination.

The substrate 250 can be a rigid structural component (e.g., a camera, a fiber optic faceplate, a microscope slide, a mirror) that causes a microwell array article to be inflexible or to retain structural memory. By coupling the microwell array article to a rigid substrate, the article can retain a shape that is optically interrogatable. The step of coupling the microwell array article to a rigid substrate is carried out by contacting the article directly to the substrate or by coating either the article and/or the rigid substrate with a bonding agent and then contacting the article/bonding agent to the substrate or substrate/bonding agent to the article. The result of the coupling step will be to cause the microwell array article to be attached to a rigid substrate, preferably such that it does not rotate, bubble, warp, curl, tear, or otherwise deform in a manner which adversely influences the ability to optically interrogate the microwells or which adversely influences the flow of fluids over the article and selected microwell locations therein.

A bonding agent useful in the adhering step of the method of the disclosure can be any substance that is capable of securing the attachment of the microwell array article to the substrate without adversely influencing the ability to optically interrogate the microwells and which does not cause the adverse degradation of the substrate or the microwell array article. As will be appreciated by one skilled in the art, when the article is coated with the bonding agent, the back surface of the article will be coated; that is, the surface coated with the bonding agent is the surface of the article not containing the formed features such as microwells. Suitable bonding agents include, but are not limited to, liquid epoxies; glues or adhesives. Preferably, a pressure sensitive adhesive is used.

A rigid substrate will either substantially prevent the microwell array article from deforming or will, upon deformation of the article, cause the article to substantially return to the article's intended shape. As will be recognized by one skilled in the art, "substantially prevent", "substantially return", and like terms refer to structural properties where the shape of the structure is maintained or reinstated in such a way as to permit the desired optical interrogation of the microwell arrays, in accordance with the methods taught and cited herein. In some embodiments, a rigid substrate is flat or planar such that substantially all microwells of an array can be accurately and simultaneously detected. An exemplary rigid substrate is a glass slide. In addition, the rigid substrate can serve to keep the article in a planar or flat configuration. As is known in the art, many detection techniques, for example, fluorescence detection, rely on very shallow depth of field detection methods using, for example, CCD cameras and confocal microscopes. Since many flexible articles cannot be made sufficiently flat or planar for such detection methods, a rigid substrate is used to maintain the article in a flat or planar configuration.

A rigid substrate can be formed from any of a variety of materials and will be selected according to the desired properties of the rigid substrate, including, but not limited to the above-discussed structural properties and other structural properties such as flatness, strength, stiffness, thickness, low thermal expansion coefficient, optical properties and chemical properties such as microstructured layer compatibility. For example, a rigid structure can be selected to have optical properties that include, but are not limited to having low autofluorescence, or being transparent, selectively transparent, having a selected refractive index, absorptive, selectively absorptive, opaque or reflective. In addition, a metal or metal-coated rigid structure can be employed to enhance signal collection from the arrays.

Compositions for a rigid substrate which demonstrate the above properties include metals, such as aluminum, iron, steel, various alloys, and the like; ceramics; composites such as fiberglass; silicon or other semiconductor materials; glass; rigid plastics or polymers; and the like.

Figure 2B:
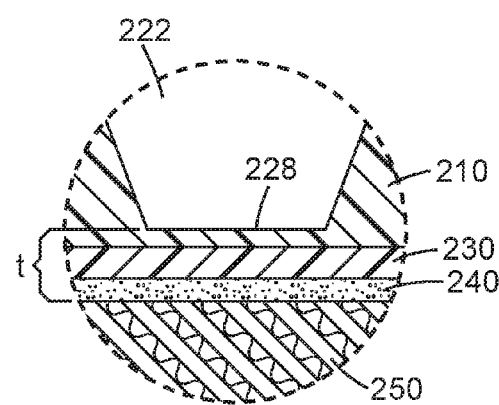
FIG. 2B is a cross-sectional view showing detail of a portion of the microwell array article of FIG. 2A.

FIG. 2B is an enlarged view of one of the microwells 222 of the microwell array article 200 of FIG. 2A. FIG. 2B shows the microstructured layer 210 comprising microwells 222 with a bottom wall 228. Also shown are the optically-transmissive flexible layer 230, optional adhesive layer 240 and optional substrate 250. The "t" indicates the minimum distance a signal must cross in order to be received by an optical device (not shown) coupled to the bottom surface of the microwell array article 200. In order for an optical signal to be detected by an optical device coupled to the bottom or the microwell array article 200, the signal must pass through the bottom wall 228, the optically-transmissive flexible layer 230, and the adhesive layer 240, if present. Thus, each of the bottom wall 228, the optically-transmissive flexible layer, and the adhesive layer 240, if present, must be transmissive to the wavelength or wavelengths of light to be detected.

Once made, the articles of the disclosure find use in a number of applications. In a preferred embodiment, the articles are used to probe a sample solution for the presence or absence of a target sequence, including the quantitation of the amount of target sequence present. In another preferred embodiment, the articles are used to determine a nucleic acid sequence.

The articles of the disclosure are useful for any of a variety of nucleic acid assays including SNP identification, sequencing, amplification, hybridization, genotyping, nucleic acid quantitation, and the like. Methods for carrying out such assays are taught in, for example, U.S. Patent Application Publication No. US 2006/0228722 and PCT International Publication No. WO 03/016868, each of which is herein incorporated by reference in its entirety.

Process for Making Flexible Microwell Arrays

The present disclosure provides a process for making flexible microwell array articles. The process comprises casting a curable resin composition onto a microstructured tool, curing the resin composition, and removing the resultant article from the tool. Similar processes are described in U.S. Pat. Nos. 5,175,030; 5,183,597; 5,384,571; 5,691,846; and 6,778,336; and in PCT Publication No. WO 9511464, each of which is incorporated herein by reference in its entirety. Briefly summarizing, the process for making such microwell array articles comprises the steps of:

a) providing
- a tool having a molding surface with a plurality of projections extending therefrom suitable for forming the microstructure elements (e.g., microwells);
- a flowable, curable resin composition; and
- an optically-transmissive flexible layer having first and second major surfaces, wherein the first major surface of the optically-transmissive flexible layer is surface-treated to promote adhesion to a cured resin composition, wherein the thickness of the optically-transmissive flexible layer is about 50 μm or less;

b) applying to the molding surface a volume of the resin composition suitable for forming the desired microstructure elements;

c) contacting the resin composition with the first major surface of the optically-transmissive flexible layer;

d) curing the resin composition while in contact with the flexible layer to form a microwell array article comprising a cured microstructured layer bonded to the flexible layer, and e) removing the microwell array article from the tool.

The tool should be such that the projections will not deform undesirably during fabrication of the microwell array article, and such that the microwell array can be separated therefrom after curing. Illustrative examples of substrates known to be useful for forming tools for replication of microwell array articles include materials that can be directly machined. Such materials preferably machine cleanly without burr formation, exhibit low ductility and low graininess, and maintain dimensional accuracy after formation of the projections. A variety of machinable plastics (including both thermoset and thermoplastic materials), e.g., acrylics, and machinable metals, preferably nonferrous, e.g., aluminum, brass, copper, and nickel are known. In many instances, it may be desired to use a first or later generation replicate of a machined or shaped surface as the tool (i.e., the member on which the disclosed microwell arrays are formed). Depending upon the tool used and the nature of the resin composition, the cured microwell array may separate from the tool readily or a parting layer may be necessary to achieve desired separation characteristics. Illustrative examples of parting layer materials include an induced surface oxidation layer, an intermediate thin metallic coating, chemical silvering, and/or combinations of different materials or coatings that create a low energy surface, such as silicones or fluorinated materials, for example. If desired, suitable agents may be incorporated into the resin composition to achieve desired separation characteristics.

As discussed above, the tool can be made from polymeric, metallic, composite, or ceramic materials. In some embodiments, curing of the resin will be performed by applying radiation through the tool. In such instances, the tool should be sufficiently transparent to permit irradiation of the resin there through. Illustrative examples of materials from which tools for such embodiments can be made include polyimide, polyacrylate, polyolefin, polycarbonates, and cured urethane acrylates. Metal tools are typically preferred, however, as they can be formed in desired shapes, are durable, and also can provide excellent optical surfaces in the substrate.

A flowable resin is applied to the molding surface of the tool. The resin should be such that it flows, optionally with applied vacuum, pressure, or mechanical means, into areas and/or cavities in the molding surface. It is preferably applied in sufficient quantity that it at least substantially fills the cavities and/or surrounds projections on the molding surface.

The method of the disclosure also includes a step of releasing the microwell arrays from the surface of the template structure. Generally, the step of removing the moldable material from the surface of the template structure will be carried out in such a way as to permit the moldable material to maintain a shape that is fully complementary to the template structure, and thus, the moldable material is removed from the surface of the template structure in the form of the microstructured layer.

Although the microwell array articles are characterized as having substantially unchanged features, it will be understood that the articles are not required to be rigid or retain structural memory beyond that of maintaining the shape of the features. The flexible microwell array articles can be stored in a compact form, such as in rolled form on a spool, as stacked sheets, or any other configuration for convenient storage.

Figure 5:
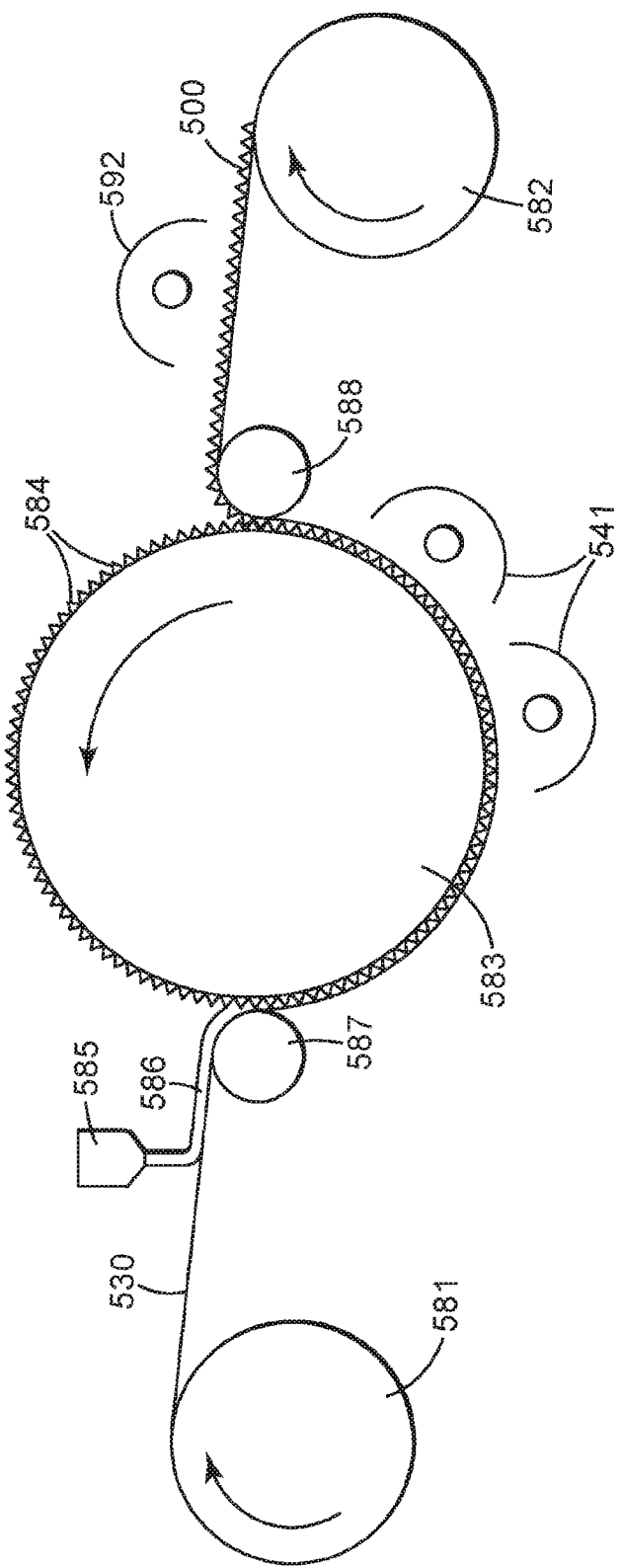
FIG. 5 is a schematic side view of one embodiment of a process for making a microwell array article according to the present disclosure.

FIG. 5 shows an exemplary apparatus for making microwell array articles according to the present disclosure. An optically-transmissible flexible layer 530 (e.g., a polymeric film) is threaded from an unwind idler 581, over a first nip roller 587, around a portion of a patterned tool roll 583 comprising microstructured projections 584, around a portion of a second nip roller 588, and onto a rewind idler 582.

A resin composition 586 is cast from a resin hopper 585 directly onto the optically transmissible flexible layer 530 at a location proximate a patterned tool roll 583. The resin/flexible layer combination is then contacted with the patterned tool roll 583 with pressure being applied through appropriate setting (described below) of first nip roller 587. Pressure applied to the first nip roller 587 serves to control the amount of resin extending between the microstructured projections 584 of patterned tool roll 583 and the optically-transmissive flexible layer 530, allowing control of the thickness of the bottom wall of the microwells formed by the microstructured projections 584. The resin composition 586 is cured by exposure to actinic radiation from a first radiation source 541, which may include a plurality of radiation-emitting bulbs, for example. The cured microwell array article 500 is pulled out of the patterned tool roll 583 at second nip roller 588 and collected onto the rewind idler 582. In some embodiments, an optional second radiation source 592 is positioned to direct radiation onto the microstructured side of the microwell array article 500 to complete the curing process.

In some embodiments, the patterned tool roll 583 may be heated to modulate the viscosity of the resin composition 586, thereby providing an additional means to control the thickness of the bottom wall.

In choosing the polymeric components of composite microarray materials of the present disclosure, it is important to select compatible polymeric materials for the microstructured layer and flexible layer. A preferred aspect of compatibility is that the material of the resin composition of the microstructured layer be capable of bonding to the optically-transmissive flexible layer when cured. In certain preferred embodiments, a major surface of the optically-transmissive flexible layer is surface-treated to promote bonding with the cured polymer that forms the microstructured layer. Suitable surface treatments include, for example, radiation treatments, corona discharge treatment (e.g., air or nitrogen corona discharge), flame treatment, plasma treatment, high energy UV treatment (e.g., flashlamp treatments), and chemical priming treatment (e.g. chemical reactive coatings).

Resins selected for use in the microarray of articles preferably yield resultant products that provide highly efficient transmission of light to a detection device or system, as well as sufficient durability and chemical stability. Illustrative examples of suitable polymers include a resin selected from the group consisting of acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof. Polymers such as poly(carbonate), poly (methylmethacrylate), polyethylene terephthalate, aliphatic, polyurethane, and cross-linked acrylate such as mono- or multi-functional acrylates or acrylated epoxies, acrylated polyesters, and acrylated urethanes blended with mono- and multi-functional monomers are typically preferred.

These polymers are typically preferred for one or more of the following reasons: high thermal stability, environmental stability, and clarity, excellent release from the tooling or mold and high receptivity for receiving a coating.

Other illustrative examples of materials suitable for forming the microarray elements are reactive resin systems capable of being cross-linked by a free radical polymerization mechanism by exposure to actinic radiation, for example, electron beam, ultraviolet light, or visible light. Radiation-initiated cationically polymerizable resins also may be used. Reactive resins suitable for forming the microarray elements may be blends of photoinitiator and at least one compound bearing an acrylate group. Preferably the resin blend contains a monofunctional, a difunctional, or a polyfunctional compound to ensure formation of a cross-linked polymeric network upon irradiation. Chemical-mediated polymerizable resins may be used (e.g., these may be polymerized by thermal means with the addition of a thermal initiator such as benzoyl peroxide). U.S. Pat. Nos. 6,395,124 and 6,692,611, each of which is incorporated herein by reference in its entirety, disclose exemplary photoinitiators that are suitable for free radical initiation of polymerization using wavelengths of light that are in the visible range (e.g., longer than 400 nm).

Illustrative examples of resins that are capable of being polymerized by a free radical mechanism that can be used herein include acrylic-based resins derived from epoxies, polyesters, polyethers, and urethanes, ethylenically unsaturated compounds, aminoplast derivatives having at least one pendant acrylate group, isocyanate derivatives having at least one pendant acrylate group, epoxy resins other than acrylated epoxies, and mixtures and combinations thereof. The term acrylate is used here to encompass both acrylates and methacrylates. U.S. Pat. No. 4,576,850, which is incorporated herein by reference in its entirety, discloses examples of crosslinked resins that may be used in microwell arrays of the present disclosure.

Ethylenically unsaturated resins include both monomeric and polymeric compounds that contain atoms of carbon, hydrogen and oxygen, and optionally nitrogen, sulfur, and halogens may be used herein. Oxygen or nitrogen atoms, or both, are generally present in ether, ester, urethane, amide, and urea groups. Ethylenically unsaturated compounds preferably have a molecular weight of less than about 4,000 and preferably are esters made from the reaction of compounds films containing aliphatic monohydroxy groups, aliphatic polyhydroxy groups, and unsaturated carboxylic acids, such as acrylic acid, methacrylic acid, itaconic acid, crotonic acid, iso-crotonic acid, maleic acid, and the like. Such materials are typically readily available commercially and can be readily cross linked.

Some illustrative examples of compounds having an acrylic or methacrylic group that are suitable for use in the disclosure are listed below:

(1) Monofunctional compounds: ethylacrylate, n-butylacrylate, isobutylacrylate, 2-ethylhexylacrylate, n-hexylacrylate, n-octylacrylate, isooctyl acrylate, bornyl acrylate, tetrahydrofurfuryl acrylate, 2-phenoxyethyl acrylate, and N,N-dimethylacrylamide;

(2) Difunctional compounds: 1,4-butanediol diacrylate, 1,6-hexanediol diacrylate, neopentylglycol diacrylate, ethylene glycol diacrylate triethyleneglycol diacrylate, tetraethylene glycol diacrylate, and diethylene glycol diacrylate; and (3) Polyfunctional compounds: trimethylolpropane triacrylate, glyceroltriacrylate, pentaerythritol triacrylate, pentaerythritol tetraacrylate, and tris(2-acryloyloxyethyl)isocyanurate.

Preferably, blends of mono-, di-, and polyfunctional acrylate containing materials are used. One skilled in the art will understand that varying the ratios among these components will determine the mechanical properties of the fully cured material.

Some representative examples of other ethylenically unsaturated compounds and resins include styrene, divinylbenzene, vinyl toluene, N-vinyl formamide, N-vinyl pyrrolidone, N-vinyl caprolactam, monoallyl, polyallyl, and polymethallyl esters such as diallyl phthalate and diallyl adipate, and amides of carboxylic acids such as N,N-diallyladipamide.

Illustrative examples of photopolymerization initiators that can be blended with acrylic compounds in microwell array articles of the present disclosure include the following: benzil, methyl o-benzoate, benzoin, benzoin ethyl ether, benzoin isopropyl ether, benzoin isobutyl ether, etc., benzophenone/tertiary amine acetophenones such as 2,2-diethoxyacetophenone, benzyl methyl ketal, 1-hydroxycyclohexylphenyl ketone, 2-hydroxy-2-methyl-1-phenylpropan-1-one, 1-(4-isopropylphenyl)-2-hydroxy-2-methylpropan-1-one, 2-benzyl-2-N,N-dimethylamino-1-(4-morpholinophenyl)-1-butanone, 2,4,6-trimethylbenzoyldiphenylphosphine oxide, phenyl-bis(2,4,6-trimethylbenzoyl)phosphine oxide, 2,4,6-trimethylbenzoylphenyl phosphinate, 2-methyl-1-4 (methylthio), phenyl-2-morpholino-1-propanone, bis(2,6-dimethoxybenzoyl) (2,4,4-trimethylpentyl)phosphine oxide, etc. The compounds may be used individually or in combination.

Cationically polymerizable materials including but are not limited to materials containing epoxy and vinyl ether functional groups may be used herein. These systems are photoinitiated by onium salt initiators, such as triarylsulfonium, and diaryliodonium salts.

Preferably, the optically-transmissive flexible layer used in the method of the present disclosure is a polymeric material selected from the group consisting of PET (polyethylene terephthalate, PEN (polyethylene naphthalate), HDPE (high density polyethylene, LDPE (low density polyethylene), LLDPE (linear low density polyethylene). PET and PEN are particularly preferred, other light transmissive elastomer, and combinations thereof. Such materials typically impart desired durability, flexibility, and light transmissivity to the resultant microwell array articles, while permitting desired bonding with the microstructured layer.

The optically-transmissive flexible layer preferably comprises a polymer having a glass transition temperature greater than about 70° C. and a modulus about $3 \times 10^9$ Pa or greater. The polymer preferably is such that the optically-transmissive flexible layer retains its physical integrity under the conditions it is exposed to as the resultant microwell array is formed. Preferred polymeric materials used in the optically-transmissive flexible layer are resistant to degradation by UV light radiation so that the microarray articles can be used for applications involving fluorescence-based detection. The optically-transmissive flexible layer should be light transmissive and preferably is substantially transparent. For instance, films with a matte finish that become transparent when the resin composition is applied thereto, or that only become transparent during the fabrication process, e.g., in response to the curing conditions, are useful herein.

The optically-transmissive flexible layer may be either a single layer or multi-layer component as desired. If multi-layer, the layer to which the microstructured layer is bonded should have the properties described herein as useful in that regard with other layers not in contact with the microstructured layer having selected characteristics (e.g., antireflective, optical transmissivity) as necessary to impart desired characteristics to the resultant microwell array. Advantageously, multilayer films may impart significant structural integrity (e.g., tear-resistance) to the microwell array articles. Further, the films used in a multi-layer construction can be selected to transmit and/or reflect selected wavelengths of light.

The optically-transmissible flexible layer is preferably about 2 microns to about 50 microns thick. More preferably, the optically-transmissive flexible layer is about 4 microns to about 25 microns thick. Even more preferably, the optically-transmissive flexible layer is about 2 microns to about 12 microns thick. Preferred materials for the optically-transmissive flexible layer include polyethylene naphthalate (PEN) and polyethylene terephthalate (PET). Preferably, the optically-transmissive flexible layer is available in roll form, to be used in a process as shown in FIG. 5.

Colorants, processing aids such as antiblocking agents, releasing agents, lubricants, and other additives may be added to one or both of the microstructured layer and optically-transmissive flexible layer if desired. The colorant may comprise a dye that is dissolved in the resin composition from which the microstructured layer is formed. Alternatively, or additionally, the colorant may comprise a pigment that is uniformly dispersed in the resin from which the microstructured layer is formed. The particular colorant selected depends on the desired transmissivity (and/or non-transmissivity) for particular colors of light; colorants typically are added at about 0.01 to 5.0 weight percent. Preferred colorants do not substantially interfere with reactants or reactions that are conducted in the microwells.

The amount of a colorant added to the resin from which the microstructured layer or in a coating that is applied to the microstructured layer can be adjusted depending upon one or more of the following parameters: the light-absorbing properties of the colorant, the distance between the closest adjacent microwells, and the thickness of the bottom wall of the microwells. It will be recognized by a person of ordinary skill in the relevant art that, as the concentration of the colorant increases, the amount of light absorbed by the microstructured layer will increase.

Microstructured layers containing high concentrations of colorant will absorb relatively more light and, thus, will permit relatively closer spacing of the microwells. In these embodiments, however, the bottom wall should be proportioned relatively thinner, in order to permit the transmission of substantially all of the light from the microwell through the bottom wall.

In contrast, microstructured layers containing lower concentrations of colorant will absorb relatively less light and, thus, will require relatively greater spacing of the microwells in order to prevent light from passing laterally through the microstructured layer from one microwell to an adjacent microwell. In these embodiments, however, the bottom wall may be proportioned relatively thicker and still permit the transmission of substantially all of the light from the microwell through the bottom wall.

In some embodiments, prior to the step of contacting the molding surface of the tool with a flowable material, a releasing agent is applied to the surface of the tool. As used herein a "releasing agent" is any compound, composition, or other substance, which aids in the separation of the moldable material from the surface of the tool in forming an article. Useful releasing agents include silicone oil, polyvinyl alcohol, fluorinated silane or other known releasing agent. Selection of the type and amount of a releasing agent will depend on several easily determinable factors such as compatibility with reactions that are conducted in the resultant microwell array, the strength of the tool, the curable resin composition, the environmental conditions of the contacting and molding process, the degree of tolerance for distortions or imperfections in the article, and the like.

In some embodiments, in addition to the steps described above, the process for making a microwell array article further comprises a step to remove (e.g., by ablation or etching) a portion of the microstructured layer and/or the optically-transmissive flexible layer. In these embodiments, the microwell array article is subjected to a process that selectively removes material from at least one surface (e.g., the upper surface, the lower surface, or the upper and lower surfaces) of the microwell array article.

Thus, in some embodiments, wherein the ablation or etching step is applied only to the upper surface of the article, the relatively thin bottom wall of each microwell can be selectively removed from the article, thereby causing the optically-transmissive flexible layer to form the bottom of each microwell in the array. Advantageously, this process can provide for better recovery of light transmitted from the interior of individual microwells, especially when high concentrations of colorant are used.

Figure 3A:
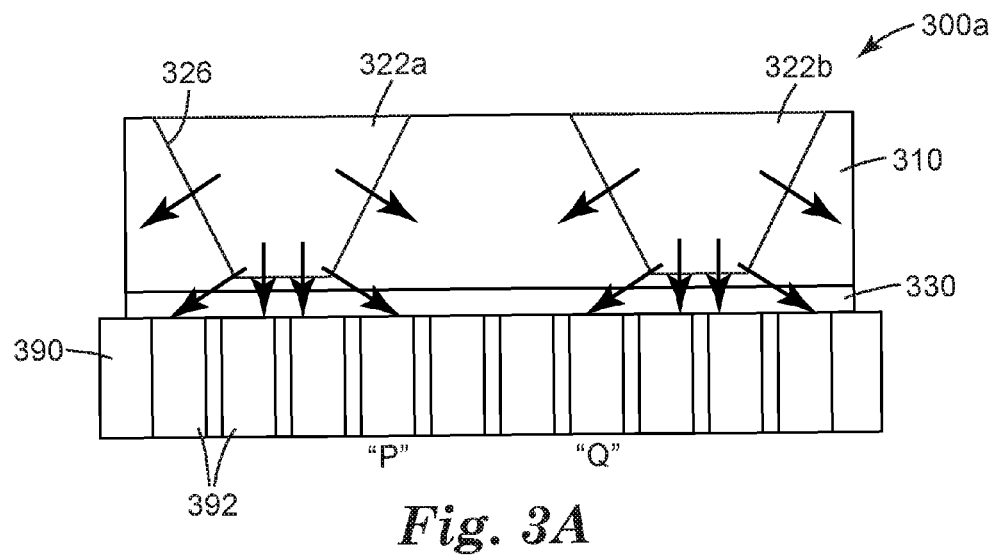
FIG. 3A is a cross-sectional schematic view of one embodiment of a microwell array article, with a relatively thin optical path extending from the microwells to an optical device.
Figure 3B:
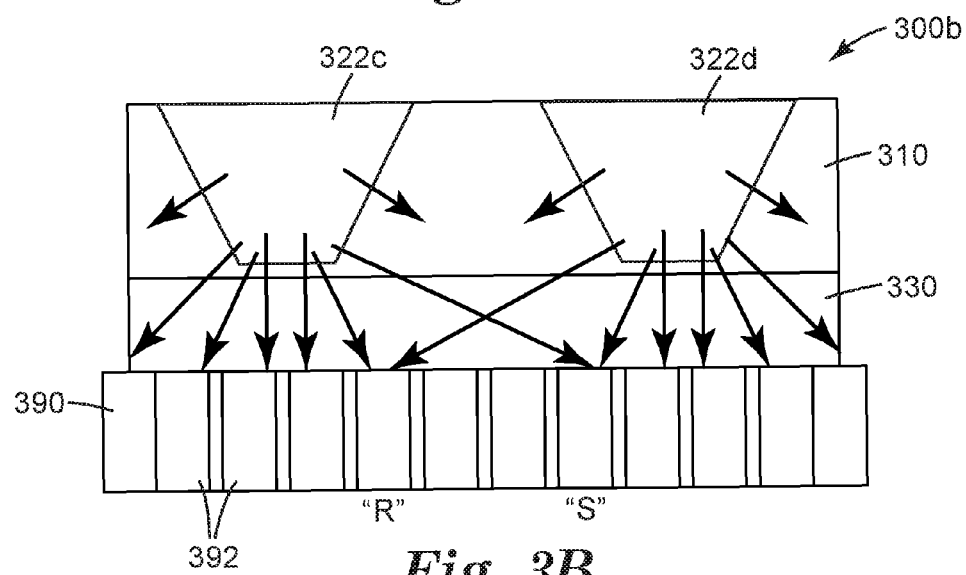
FIG. 3B is a cross-sectional schematic view of one embodiment of a microwell array article, with a relatively thick optical path extending from the microwells to an optical device.

In alternative embodiments, wherein the ablation or etching step is applied only to the lower surface of the article, a portion of a relatively thick optically-transmissive flexible layer can be uniformly removed to produce a thinner optically-transmissive flexible layer. Advantageously, this process can provide for less optical cross-talk, as shown in FIGS. 3A and 3B and described herein.

When both the upper and lower surfaces of the article are subjected to the ablation process, the resultant microwell array articles can have increased light transmission from the microwells and decreased optical cross-talk.

Processes for controllably ablating thin layers of flexible polymeric films are known in the art and include, for example, plasma treatment, reactive ion etching, laser ablation, or chemical etching (e.g., using hydrolytic agents, such as a solution containing 40% w/v potassium hydroxide and 20% w/v ethanolamine to chemically etch PET film).

Thin Film Coatings

The surface of the array substrate may be coated with a thin layer of material to enhance the properties and functions of the microwells. The coating may protect the contents of the solution in the reaction chamber from the deleterious effects of the array substrate, without compromising the utility or ease of fabrication of the array. The coating may also provide a uniform surface composition allowing for uniform modification of the reaction chamber surface (e.g., with a monolayer).

The present disclosure provides for the application of a coating to the array substrate. Such coatings are designed to improve the properties and functions of the array, including compatibility of the reaction mixture or assay solution. The coating may provide a barrier between the solution contained in the microwell and the substrate, and prevents both leaching of the substrate material into the solution and contact of the contents in the microwell with the substrate.

In some embodiments, the substrate is coated with a thin film comprised of a material typically known to be compatible with components found in assay solutions and chemical reaction mixtures. In one embodiment, the coating may be impermeable to water. In another embodiment, the coating can provide for a uniform surface composition. Preferably, the coating is optically transparent and such transparency facilitates detection.

Other desirable properties of the coating include durability, compatibility with the substrate materials, well-understood deposition parameters, and resistance to relatively high temperatures. In one embodiment, the coating is adhesive to glassy materials. The coating may preferably minimize non-specific absorption of macromolecules to the side and bottom walls of the microwells. In one embodiment, the coating allows for easy attachment of reactants (e.g. proteins and nucleic acids) and does not negatively affect the activity of immobilized reactants, but rather in some instances, can increase their stability.

The coating may be deposited on the surface of the array (i.e., the area lying outside the microwells), on the bottom walls of a microwell, and/or on the side walls of a microwell. In one embodiment, the thin film is deposited on the entire substrate. In another embodiment, the coating is deposited on the surface of the array. In a further embodiment, the coating is deposited on the bottom wall of each microwell. In a further embodiment, the coating is deposited on the side walls of each microwell. In some embodiments, the coating is deposited on the bottom wall and side walls of each microwell and on the surface of the substrate.

The term "coating" refers to a relatively thin composition (e.g., a film) with a thickness that is significantly smaller than other characteristic dimensions of the substrate. In a preferred embodiment, the coating is uniform and conformal to the microstructured layer, with a thickness of about 25 to about 1000 nanometers. The thickness of the coating may be non-uniform over the surface of the array. For example, in one embodiment, the thickness of the thin film coating can be about 50-500 nm on the top surface of the array substrate; about 25-250 nm on the side walls of the microwells, and about 50-500 nm on the bottom walls of the microwells.

Many different types of materials can be used as a coating. The composition of a coating material will depend on the array substrate, the application, and the method of coating deposition. In one embodiment, a coating is a polymer (e.g., an inorganic polymer). A coating can be a non-metal oxide (e.g. silicon dioxide ($SiO_2$)). Other coatings may be, for example, a metal alloy, a metal or semi-conductor oxide, nitride, carbide or boride. Other materials for coating the substrate may include gold layers (e.g. 24 karat gold). Many coatings are commercially available.

Coating materials also include those systems used to attach a polypeptide or polynucleotide to a substrate. Organosilane reagents, which allow for direct covalent coupling of proteins via amino, sulfhydryl or carboxyl groups, can be used to coat the array substrate. Additional coating substances include photoreactive linkers (e.g. photobiotin).

Other coating materials include polymeric materials such as hydrophilic polymer gels (e.g., polyacrylamide and polysaccharides), which may be polymerized directly on the surface of the substrate or polymer chains that are covalently attached to the substrate. Other coating materials also include passively-adsorbed layers (e.g., biotin-binding proteins). The substrate can also be coated with an epoxide which allows the coupling of reagents via an amine linkage.

In a preferred embodiment, the coating is $SiO_2$. The substrate can be coated with a film coating of $SiO_2$. Film coatings of $SiO_2$ are optically transparent, function efficiently as a water barrier in thicknesses down to 10 nm, adhere to glassy materials, and withstand harsh cleaning procedures and relatively high temperatures. Further, the surface properties of $SiO_2$ are well known, as are methods for modifying these properties. Further, $SiO_2$ has been shown to be compatible with microscale biological assays such as polymerase chain reaction ("PCR"), for example.

Coated microwells can be biologically or chemically functionalized. Any of the film materials discussed can be derivatized with one or more functional groups, commonly known in the art for the immobilization of polypeptides and/or polynucleotides, e.g. metal chelating groups (e.g. nitrilo, triacetic acid, iminodiacetic acid, pentadentate chelator). In one embodiment, the coated microwell is modified to contain functional groups that can be used to attach or capture, either covalently or non-covalently, reactants or analytes to the coated walls of the microwell. "Chemically-functionalized microwells" in this context include, but are not limited to, the addition of functional groups including amino groups, carboxy groups, oxo groups and thiol groups, that can be attached to the coated surface of the microwell and be used to attach or capture reactants or analytes on the same surface. Biological modifications of the coated microwell include, for example, the attachment of binding ligands or binding partner pairs, including but not limited to, antigen/antibody pairs, enzyme/substrate or enzyme/inhibitor pairs, receptor-ligand pairs, carbohydrates and their binding partners (lectins, etc.).

Method of Preparing a Flexible Microwell Array for Microanalysis

The present disclosure provides a method to prepare a flexible microwell array article for microanalysis. The method comprises providing an article that includes first and second protective layers with a flexible microwell array comprising an adhesive layer disposed there between. The method further comprises providing a component of an optical system. The method further comprises pulling the second protective layer away from the microwell array such that the second protective layer is detached from the microwell array and/or the first protective layer. The method further comprises applying the lower major surface of the microwell array to the optical system component.

Figure 8A:
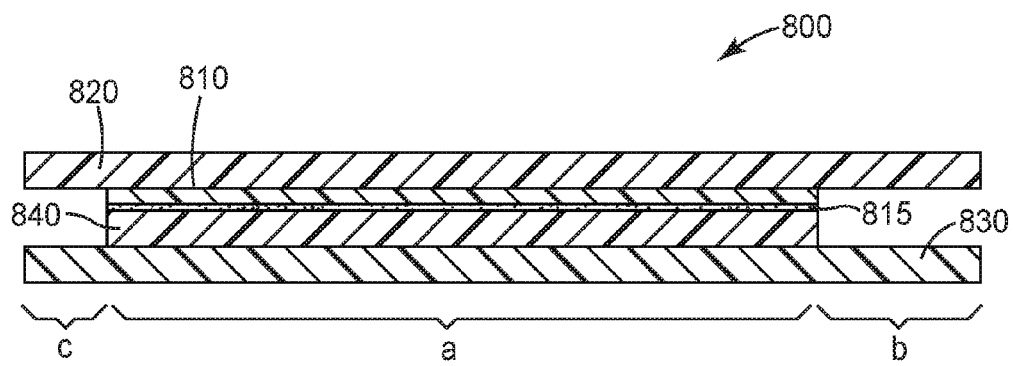
FIG. 8A is a side view of one embodiment of a carrier article with a flexible microwell array according to the present disclosure.

FIG. 8A shows one embodiment of a microwell article comprising protective layers. The article 800 comprises a flexible microwell array 810 that includes an adhesive layer 815 on the major surface of the microwell array article 810 opposite the major surface that includes the microwells (microwells are not shown in FIGS. 8A-8F). A first protective layer 820 is coupled to the microwell array 810 on the major surface opposite the adhesive layer 815. A shielding element 840 is coupled to the adhesive layer 815. A second protective layer 830 is coupled to the shielding element 840. FIG. 8A shows the body region ("a"), which is substantially coextensive with the microwell array 810, of the first and second protective layers (820 and 830, respectively). Extending beyond one edge of the microwell array 810 is the tab region ("b") of the first and second protective layers (820 and 830, respectively). Extending beyond another edge of the microwell array 810 is a margin area ("c"). The margin area "c", is a portion of the article outside of the tab region where the peripheral boundaries of the first and second protective layers overlap and extend beyond the peripheral boundary of the microwell array.

Figure 8B:
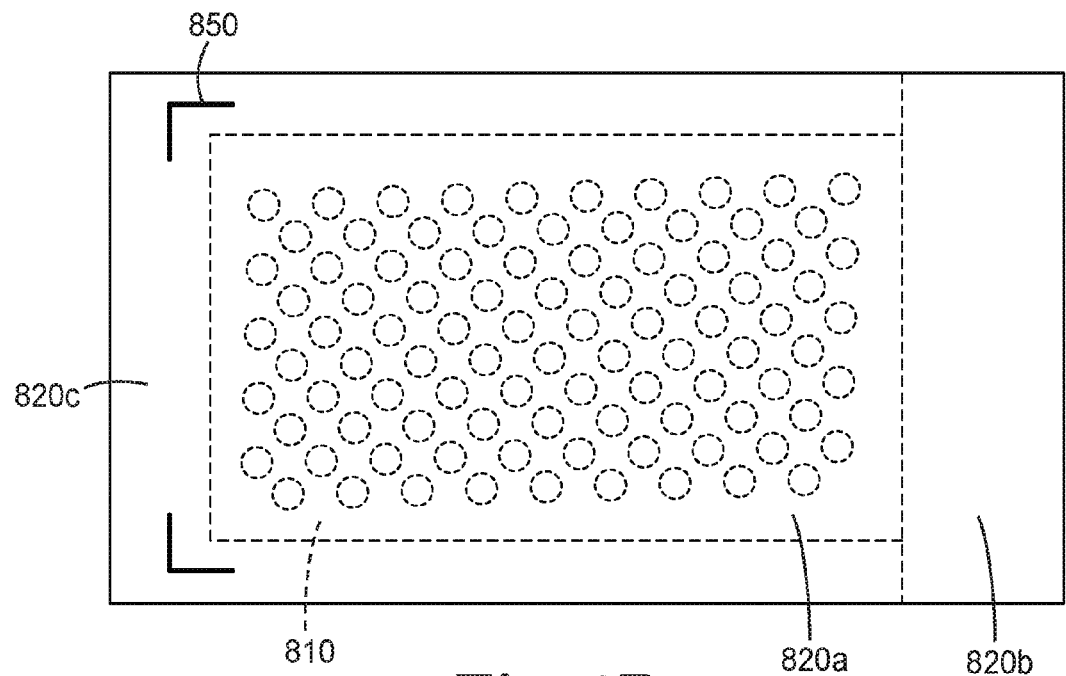
FIG. 8B is a top view of the carrier article of FIG. 8A.

FIG. 8B shows a top view of the article of FIG. 8B. FIG. 8B illustrates that the first protective layer body region 820a of the article 800 is substantially coextensive with the microwell array 810, thereby forming a covering over the microwells 812. The first protective layer tab region 820b extends from a portion of the first protective layer body region 820a. Like the tab region 820b, the first protective layer margin area 820c extends from the first protective layer body region 820a beyond the peripheral boundary of the microwell array 810. Also shown in FIG. 8B are alignment indicia 850. Alignment indicia can be any marking or combination of markings (e.g., lines, dots, lettering, symbols, or the like) that can serve as a point of reference to properly align the microwell array 815 with a component of an optical system (e.g., a camera, a fiber optic array, a line scanner (not shown)).

Figure 9A:
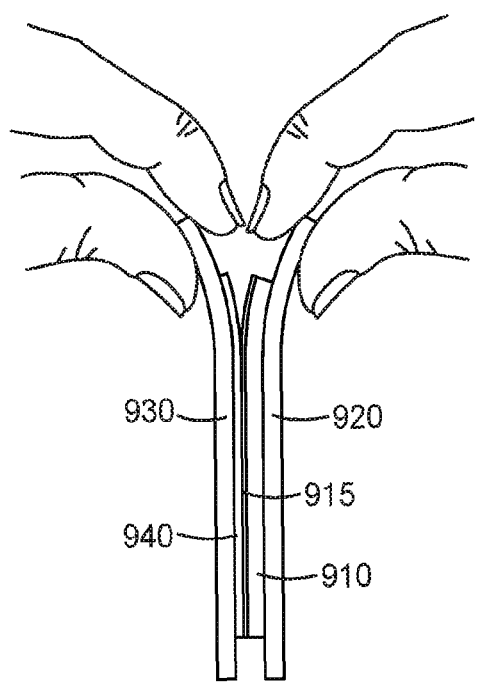
FIGS. 9A-9F are side views of the steps of a process to prepare a microwell array for microanalyses according to the present disclosure.

FIGS. 9A-9F illustrate one embodiment of the method to prepare a flexible microwell array for microanalysis. FIG. 9A shows an article 900 comprising a flexible microwell array 910 according to the article of FIG. 9A. The microwell array 910 comprises an adhesive layer 915. The article further comprises a shielding element 940 releasably bonded to the adhesive layer 915, a first protective layer 920 releasably bonded to the microwell array 910, and a second protective layer 930 releasably bonded to the shielding element 940. In this step, the first protective layer 920 and second protective layer 930 are grasped and generally pulled in opposing directions to separate the layers.

Figure 9B:
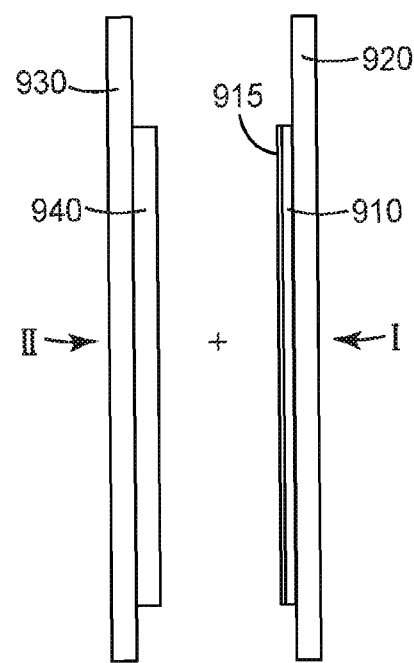

FIG. 9B shows the two components (I and II) resulting from the separation of the protective layers during the step described in FIG. 9A. In this embodiment, component I comprises the first protective layer 920 with the microwell array 910 comprising an adhesive layer 915 bonded thereto. Component II comprises the second protective layer 930 with the shielding layer 940 bonded thereto. Thus, in this embodiment, the peel adhesion strength of the bond between the first protective layer 920 and the microwell array 910, the peel adhesion strength of the bond between the microwell array 910 and the adhesive layer 915, and the peel adhesion strength of the bond between the second protective layer 930 and the shielding element 940 are all greater than the peel adhesion strength of the bond between the shielding element 940 and the adhesive layer 915. In an alternative embodiment (not shown), the relative peel adhesion strengths can be selected such that when the first and second protective layers (920 and 930, respectively) are separated, the shielding element 940 remains bonded to the adhesive layer 915 rather than the second protective layer 930.

Figure 9C:
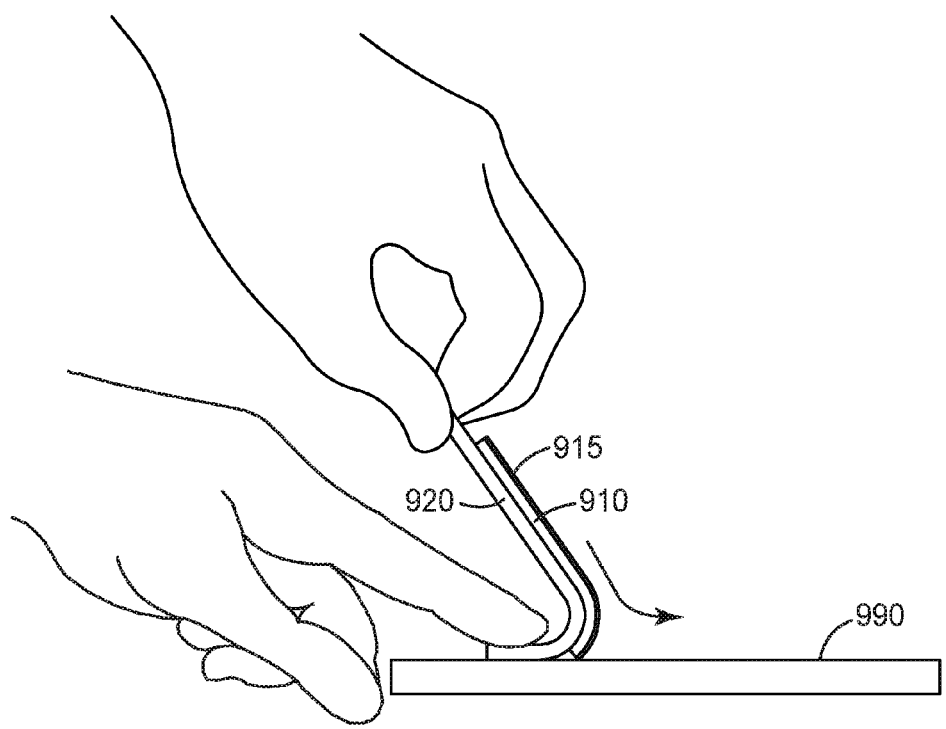

The microwell array 910 is then applied to a component 990 of an optical system, as shown in FIG. 9C. In a preferred embodiment, a peripheral portion (e.g., an edge) of the adhesive layer 915 of the microwell array 910 is contacted with the optical component 990 (e.g., a camera, a fiber optic bindle). The remainder of the adhesive layer 915 is contacted with the component 990, preferably, by bending the component I into a slightly curved shape and "rolling" the adhesive layer 915 of the curved flexible microwell array 910 in the direction of the arrow onto the component 990 in a smooth motion to avoid the formation of wrinkles and/or the entrainment of air bubbles between the adhesive layer 915 and the microwell array 910.

Figure 9D:
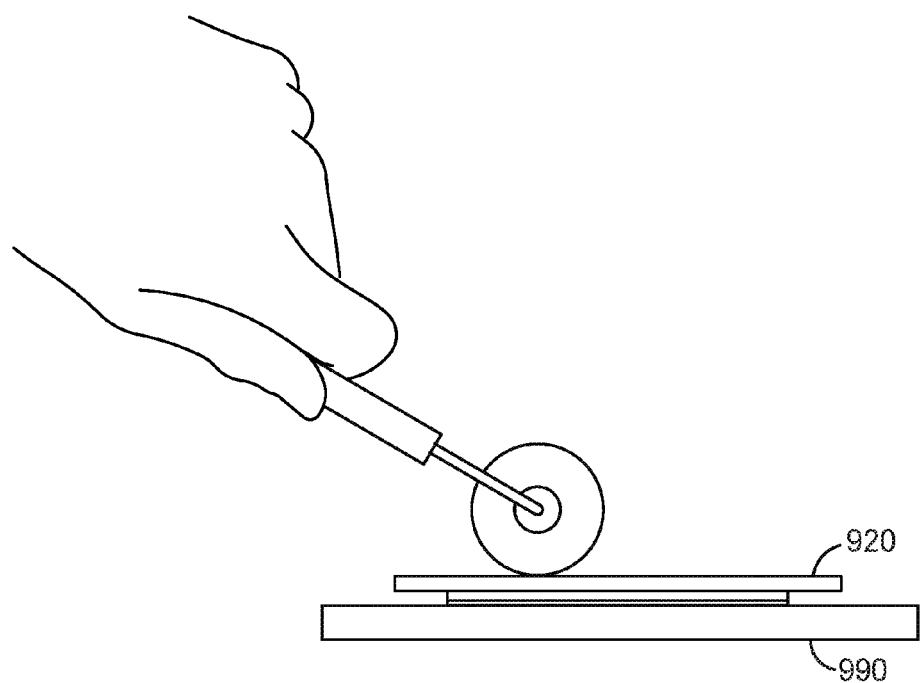

After contacting the microwell array 910 with the optical component 990, the microwell array 910 can be processed to achieve a substantially uniform, flat surface on the optical component 990. FIG. 9D shows how, optionally, a roller 995 can be contacted to the exposed surface of the first protective layer 920 to provide uniform contact between the microwell array 910 and the optical component 990. This process can further provide more uniform optical properties (e.g., depth of field, depth of focus, adhesive thickness) for imaging each reaction site in the microwell array 910.

Figure 9E:
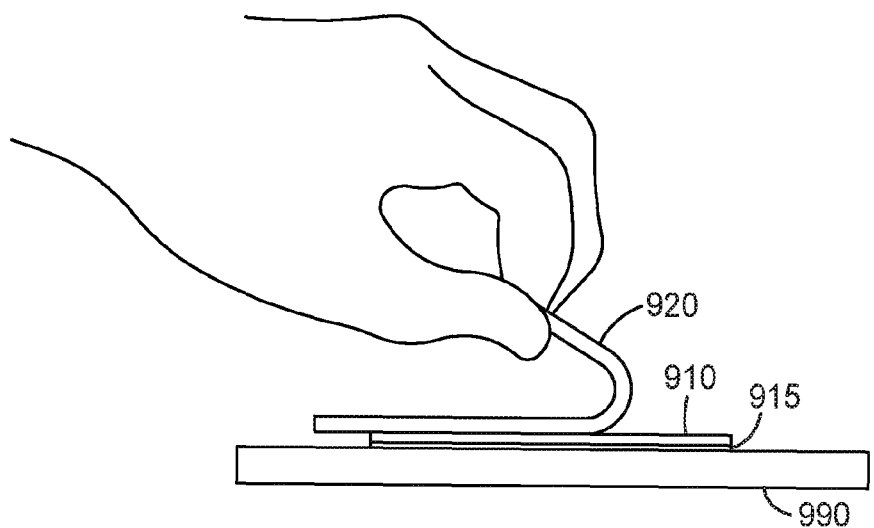
Figure 9F:
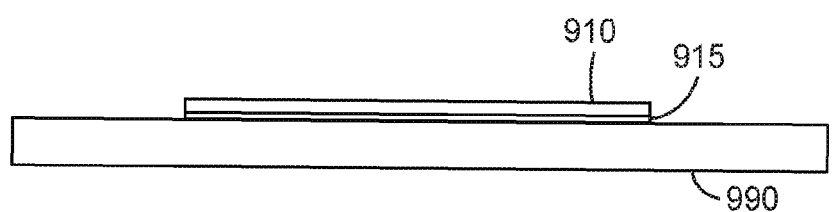

The first protective layer 920 is removed from the microwell array 910 to expose the reactive sites for microanalyses, as shown in FIG. 9E. Optionally, a roller may be contacted to the surface of the microwell array 910, as described above. FIG. 9F shows the microwell array 910 optically coupled via adhesive 915 to the optical component 990 for microanalyses.

Method of Detecting an Analyte

The present disclosure provides methods to detect an analyte. A method of detecting an analyte comprises providing a sample suspected of containing an analyte, an assay reagent for the optical detection of the analyte, an optical detection system, and a microwell array article according to the present disclosure. The method further comprises contacting the sample and the assay reagent in at least one microwells under conditions suitable to detect the analyte, if present, in the at least one microwells. The method further comprises using the optical detection system to detect the presence or absence of the analyte in a microwell.

Suitable conditions include a variety of assay conditions known in the art. Nonlimiting examples of assay conditions include assay conditions for the detection of binding partners (e.g., receptor-ligand reactions; antigen-antibody reactions, for example; and nucleic acid hybridization reactions) as well as assay conditions suitable for an enzyme reaction (e.g., nucleic acid amplification, nucleic acid sequencing). Microvolume assays performed in microwell arrays are described in, for example, U.S. Pat. No. 6,942,968; and PCT International Publication No. WO 03/016868; each of which is incorporated herein by reference in its entirety.

The assay reagent may comprise a probe (e.g., a protein or a polynucleotide). The probe may be a labeled probe. The probe may be labeled with any of a variety of optically-detectable labels that are known in the art. The assay reagent may comprise an enzyme. Nonlimiting examples of enzymes used in optical detection for biological assays include DNA polymerase, thermonuclease, Taq polymerase, and alkaline phosphatase. The assay reagent may comprise an enzyme substrate. The enzyme substrate may be suitable for a reaction that can be detected optically. In some embodiments, the enzyme substrate is a fluorogenic enzyme substrate. In some embodiments, the enzyme substrate is a lumigenic enzyme substrate. In some embodiments, the enzyme substrate may react with a first enzyme to produce a product that reacts with a second enzyme in a fluorometric or lumimetric reaction.

In some embodiments, one or more of the biological assay components of the biological assay is attached to a particle (e.g., a microparticle, a nanoparticle, a bead). The assay component may be the sample suspected of containing an analyte (e.g., the analyte is synthesized or captured and/or concentrated onto a particle). The assay component may be a binding partner (e.g. a polypeptide, antibody, or polynucleotide probe that selectively binds to the analyte). The assay component may be an enzyme. Suitable particle compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used.

Generally in this embodiment, the particles are non-covalently associated in the microwells, although the microwells may additionally be chemically functionalized as described herein. Cross-linking agents may be used, or a physical barrier may be used, i.e. a film or membrane over the particles, to prevent the particles from migrating out of and/or between microwells.

The particles need not be spherical. Irregular particles may be used. In addition, the particles may be porous, thus increasing the surface area of the particle available for either bioactive agent attachment or analyte attachment. The particle sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

In some embodiments, each particle comprises a target analyte or a bioactive agent, although as will be appreciated by those in the art, there may be some particles which do not contain a target analyte or a bioactive agent, depending on the synthetic methods. Alternatively, as described herein, in some embodiments it is desirable that a population of particles does not contain a bioactive agent or a target analyte. "Candidate bioactive agent" or "bioactive agent" or "chemical functionality" or "binding ligand", as used herein, describes any molecule, e.g., protein, oligopeptide, small organic molecule, coordination complex, polysaccharide, polynucleotide, etc. which can be attached to the solid supports of the disclosure. It should be understood that the articles of the disclosure have two primary uses. In a preferred embodiment, as is more fully outlined below, the compositions are used to detect the presence or absence of a particular target analyte; for example, the presence or absence of a particular nucleotide sequence or a particular protein, such as an enzyme, an antibody or an antigen. In an alternate preferred embodiment, the microwell arrays are used to screen bioactive agents, i.e. drug candidates, for binding to a particular target analyte.

As will be appreciated by those in the art, the biological agents may either be synthesized directly on the particles, or they may be made and then attached to the particles after synthesis. In a preferred embodiment, linkers are used to attach the biological agents to the particles, to allow good attachment, sufficient flexibility to allow good interaction with the target molecule, and to avoid undesirable binding reactions. In a preferred embodiment, the biological agents are synthesized directly on the beads. As is known in the art, many classes of chemical compounds are currently synthesized on solid supports, including beads, such as peptides, organic moieties, and nucleic acids.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, microparticles may be used that have surface chemistries that facilitate the attachment of the desired functionality by the user. Some examples of these surface chemistries for microparticles include, but are not limited to, amino groups including aliphatic and aromatic amines, carboxylic acids, aldehydes, amides, chloromethyl groups, hydrazide, hydroxyl groups, sulfonates and sulfates.

In some embodiments, the particles in each well of the microarray may comprise identical or substantially identical bioactive agents. In an alternative embodiment, the microarray may comprise a population of particles with related, but nonidentical bioactive agents (e.g., fragments of a gene or a chromosome). In some embodiments, the microarray may comprise a population of particles with random bioactive agents.

It should be noted that not all sites of an array may comprise a microparticle; that is, there may be some sites on the substrate surface which are empty. In addition, there may be some sites that contain more than one bead.

In general, either direct or indirect detection of the analyte or target analyte can be performed. "Direct" detection, as used herein, involves the detection of a signal (e.g., a, fluorescent or luminescent signal) as a result of a direct interaction (e.g., binding) of the analyte with a binding partner (e.g., an antibody, a polynucleotide) or a reaction component (e.g., an enzyme or an enzyme substrate). Nonlimiting examples of direct detection include the detection of a labeled (e.g., fluorescently labeled) antibody that selectively binds to a target analyte, the detection of a labeled polynucleotide that selectively hybridizes to a target analyte, and the detection of an enzyme product (e.g., a chromatic, fluorescent, or luminescent product) resulting from a reaction of the enzyme with the target analyte. Methods for labeling various binding partners and methods for detecting the labeled molecules are well known in the art.

"Indirect" detection involves, for example the detection of a signal (e.g., a chromatic, fluorescent, or luminescent signal) that is generated as a result of the interaction (e.g., binding) of the analyte with an unlabeled "primary" binding partner (e.g., an antibody, a polynucleotide), followed by the interaction of the primary binding partner with a labeled "secondary" binding partner. In some embodiments, indirect detection may involve the detection of a reaction product (e.g., an enzyme reaction product) or that is generated, for example, as a result of an enzyme-labeled binding partner selectively binding to the analyte or as a result of a secondary enzyme reaction that is catalyzed by the interaction of the target analyte with a primary enzyme (see Reaction Schemes I and II).

Reaction Scheme I

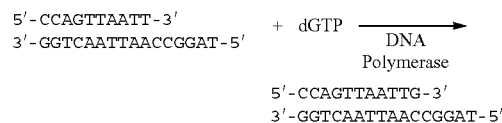

Reaction Scheme II

Reaction Scheme I shows a primary enzyme reaction involving two substrates (a double-stranded polynucleotide having a single-stranded region, and deoxyguanosine triphosphate), an enzyme catalyst (DNA polymerase), and two products (a double-stranded polynucleotide to which the guanosine dexoyribonucleotide was added, and pyrophosphate (PPi)). Reaction Scheme II shows a secondary enzyme reaction that can result from the reaction shown in Reaction Scheme I. In the secondary reaction, the enzyme (luciferase) reacts with the substrates (pyrophosphate and luciferin) to generate a chemical product (phosphate) and a detectable signal (light).

In some embodiments, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes. Secondary labels include, but are not limited to, one of a binding partner pair; chemically modifiable moieties; nuclease inhibitors, enzymes such as horseradish peroxidase, alkaline phosphatases, luciferases, etc.

In some embodiments, the secondary label is a binding partner pair. For example, the label may be a hapten or antigen, which will bind its binding partner. In some embodiments, the binding partner can be attached to a solid support, for example to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the two components of a binding pair is attached to an NTP for incorporation into a primer. Nonlimiting examples of binding partner pairs include biotin (or imino-biotin) and streptavidin.

Generally, in an assay to detect a binding partner (e.g., an antigen-antibody reaction, a receptor-ligand reaction) a sample containing a target analyte (whether for detection of the target analyte or screening for binding partners of the target analyte) is added to the array, under conditions suitable for binding of the target analyte to a corresponding binding partner, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optically-detectable event.

In a preferred embodiment, a change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, the label will only be detectable in the presence of target hybridization. Thus, upon binding of the target analyte to a corresponding binding partner, there is a new optical signal generated at that site, which then may be detected.

Alternatively, in some cases, as discussed above, a reporter such as an enzyme generates a species that is either directly or indirectly optically detectable.

Furthermore, in some embodiments, a change in the optical signature may be the basis of the optical signal. For example, the interaction of some chemical target analytes with some fluorescent dyes on the beads may alter the optical signature, thus generating a different optical signal (e.g., fluorescence quenching).

As will be appreciated by those in the art, in some embodiments, the presence or absence of the target analyte may be detected using changes in other optical or nonoptical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins (e.g. albumin), detergents, etc., which may be used to facilitate optimal protein-protein binding and/or reduce non-specific or background interactions. Also reagents that otherwise improve the efficiency of the assay, such as protease inhibitors, nuclease inhibitors, antimicrobial agents, etc., may be used. The mixture of components may be added in any order that provides for the requisite binding. Various blocking and washing steps may be utilized as is known in the art.

Optical Systems

Methods of the present disclosure include the use of an optical system to detect an analyte in a microwell array article. The optical system can include an optical device (e.g., a CCD camera, a line scanner) to capture image data into transformable and/or quantifiable formats. In some embodiments, the optical device can be optically-coupled to the microwell array article. The optical system may further comprise an optical conduit (e.g., a fiber optic bundle) to carry image components from the microwell array article to an imaging device. The optical system may further comprise a processor. The processor may comprise image analysis software to analyze the image data.

Optical devices (e.g., CCD cameras) used in the method of the present disclosure will permit simultaneous detection of events in one or more microwells in a microwell array. The CCD cameras used in detection can be coupled with additional optics devices including lenses, fiber optics, image intensifiers, and the like, for amplifying, focusing, reducing or expanding the images produced in the detection methods of the disclosure. One skilled in the art will be readily able to determine the detector and optics required according to the desired screening methods and the dimensions of the microwell arrays.

Optical devices include microscopes, such as confocal microscopes, for example. Confocal microscopes used in methods of the present disclosure will permit simultaneous imaging of one or more microwells in a microarray. The confocal microscope will typically be configured for receiving an array of the present disclosure which is formatted to the dimensions of a microscope slide.

Optical devices also include raster-scanning laser devices, including those that utilize photomultiplier tube detection. Exemplary detection instruments useful with the microwell array of the disclosure are well known in the art and include, for example, the GenePix 40008 Array Scanner from Axon Instruments, Inc., GSI Scanarray 3000 from GSI Luminomics, and the like.

In one embodiment of the disclosure, the microwell array will be attached via a liquid and/or vapor tight seal to a fluid flow device. Such a fluid flow device will permit sample, solvent, probes, rinsing solutions, reacting solutions, and the like, to flow over the microwells and the microparticles thereon, if present. Thus, a fluid flow device will be capable of carrying out functions such as those disclosed above. Fluid flow devices known in the art include flow cells such as those provided by manufacturers such as Mindrum Precision, Inc., Rancho Cucamonga, Calif.; Upchurch Scientific, Oak Harbor, Wash., and 454 Life Sciences, Branford, Conn.

In a preferred embodiment of the disclosure, the microwell array is attached to a fluid flow device and positioned with respect to a detection instrument such as a confocal microscope or a CCD camera in such a way as to permit numerous iterations of sample loading, detection, rinsing, and the like, without requiring the array composition to be moved or manipulated in any manner beyond fluid flow through the fluid flow device.

The hardware used in the apparatus and detection methods of the disclosure preferably orients the microwell arrays with respect to the detector optics or to the CCD camera or other optical detection device such that substantially all discrete sites (i.e., 80% or more, preferably 90% or more, more preferably 95% or more) of an array, and, in a preferred embodiment, all arrays (i.e., 80% or more, preferably 90% or more, more preferably 95% or more), can be accurately and simultaneously detected. The present disclosure provides a microwell array that can be positioned directly on an optical device for accurate, simultaneous measurement by, for example, all microwells being oriented at the same distance from the optics or detector.

In some embodiments, the article can be optically-coupled to an imaging system. In certain embodiments, the imaging system comprises an imaging device (e.g., a CCD camera) with an image sensor density of about 10,000 image sensors per $mm^2$. In certain embodiments, the imaging system comprises a fiber optic bundle with a cross-sectional fiber density of about 100,000 optical fibers per $mm^2$. The fiber optic bundle can transmit light emitted from a microwell to an imaging device (e.g., a camera). Advantageously, the articles described herein can be manufactured such that the area comprising the bottom wall of a microwell corresponds to the area occupied by about 4 individual image sensors in said camera or about 4 individual optical fibers in said fiber optic bundle. It will be appreciated that, by minimizing the thickness of the bottom wall and the optically-transmissive flexible layer, any light transmitted through the bottom wall of a given microwell will be directed to a limited and/or predetermined number of image sensors or optical fibers proximate the bottom wall of the microwell, as shown in FIG. 3A.

Optical Isolation

The present disclosure provides for arrays of microwells that are optically isolated in an X-Y plane and optically transmissive in a Z axis. The microwells can be optically isolated by a variety of means described herein. In some embodiments, the means for optically-isolating microwells in an array comprises dispersing or dissolving a colorant in the microstructured layer. In some embodiments, the colorant is dissolved or uniformly dispersed in the material (e.g., plastic polymer) from which the microstructured layer is formed.

The colorant may be a pigment or a dye that absorbs a selected wavelength or a selected band of wavelengths (e.g., a particular color or set of colors or the entire spectrum of visible wavelengths) of light. Nonlimiting examples of suitable colorants include carbon black, fuchsin, carbazole violet, and Foron Brilliant Blue. Suitable colorants described herein belong to a variety of dye classes. Nonlimiting examples of suitable dye classes include anthraquinone dyes (e.g., 1,5-bis[(1-methylethyl)amino)]-9,10-Anthracenedione and 1-(hexylamino)-4-hydroxy-9,10-Anthracenedione); bis (trifluoromethanesulfonyl)methylene merocyanine dyes (e.g., 4-[4,4-bis[(trifluoromethyl)sulfonyl]-1,3-butadien-1-yl]-Benzenamine, 4,4'-[4,4-bis[(trifluoromethyl)sulfonyl]-1, 3-butadienylidene]bis[N,N-dimethyl-Benzenamine, and 4-[4-[4,4-bis[(trifluoromethyl)sulfonyl]-1,3-butadien-1-

Morpholine); p-(tricyanovinyl) arylamine dyes (e.g., 2-[4-(dibutylamino)phenyl]-1,1,2-Ethenetricarbonitrile); merocyanine dyes (e.g., 2-[(1-methyl-4(1H)-quinolinylidene) methyl]-5-nitro-Benzonitrile); and indoaniline (indophenol) dyes (e.g., 4-[[4-(dimethylamino)phenyl]imino]-1(4H)-Naphthalenone and 4-[[4-(diethylamino)phenyl]imino]-1 (4H)-Naphthalenone). Numerous subclasses of merocyanine dyes, with appropriate absorption spectra, are suitable as colorants according to the present disclosure.

In some embodiments, the colorant can comprise a 1-(alkylamino)-4-hydroxy-derivative of 9,10-anthracenedione. Suitable alkyl groups for the 1-alkylamino-4-hydroxy-derivatives of 9,10-anthracenedione include, for example, n-hexyl-; 3-methylbutyl-; -decamethylene-(bis); 3-methoxypropyl-; furfuryl-; n-pentyl-; cyclohexyl-; 2-ethylhexyl-; 2-heptyl-; 3-ethoxypropyl-; 3-n-butoxypropyl-; 1,1,3,3-tetramethylbutyl-; 3-methyl-2-butyl-; 3-dimethylaminopropyl-; and 1,1-dimethylethyl-groups. Advantageously, nonionic 1-(alkylamino)-derivatives of 9,10-anthracenedione that have a melting point less than about 140° C. are generally quite soluble in resin formulations described herein, thereby permitting the attainment of higher concentrations of the dyes, if needed, in the polymerized resins (e.g., acrylate resins, acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof).

The synthesis of amino-derivatives of 9,10-anthracenedione is described in U.S. Pat. No. 2,128,307; which is incorporated herein by reference in its entirety; and in Examples 73-78 herein.

In some embodiments, the colorant may be a pigment or a dye that permits the transmission of a selected wavelength or a selected band of wavelengths (e.g., ultraviolet wavelengths) of light.

In some embodiments, the colorant may be a pigment or a dye that absorbs a selected wavelength or a selected band of wavelengths (e.g., visible wavelengths) of light and permits the transmission of a different selected wavelength or a selected band of wavelengths (e.g., ultraviolet wavelengths) of light. Exemplary colorants that absorb visible wavelengths of light and permit the transmission of ultraviolet wavelengths of light are fuchsin and violet pigment 9S949D, available from Penn Color, Doylestown, Pa.

Articles of the present disclosure may include a colorant. The colorant may include a pigment, a dye, a mixture of pigments, a mixture of dyes, or a combination of any two of the foregoing. In some embodiments, the colorant comprises a nonionic colorant.

Resin compositions of the present disclosure can include a colorant. In some embodiments, the resin composition can be polymerized using actinic radiation (e.g., u.v. and/or near-u.v. wavelengths of light). Excessive absorption of the actinic radiation can reduce the efficiency of the polymerization process. Thus, in some embodiments, it may be desirable to select a colorant that does not substantially affect the polymerization process of the resin composition (e.g., a colorant that is substantially transmissive for u.v. and/or near-u.v. wavelengths).

In certain preferred embodiments, the colorant does not substantially interfere with the flow of the resin composition into and/or onto the microreplication tool. The present disclosure provides suitable intensely-colored resin compositions that are unimpeded in flow into the microreplication mold, as compared to the uncolored resin compositions.

Articles of the present disclosure may be used in a microassay to detect chemical and/or biochemical reactions that emit and/or transmit light. For example, articles of the present disclosure may be used to detect light emitted by a reaction comprising a luciferase enzyme. Various luciferase enzymes catalyze reactions that emit light in the range from about 480 nm to about 615 nm. In order to reduce or prevent lateral transmission of the emitted light from one reaction well to an adjacent reaction well, the article should comprise a colorant that substantially absorbs light in the range from about 480 nm to about 615 nm or portions of that range.

Thus, in some embodiments, it is desirable to select a colorant that is substantially transmissive for one range of wavelengths of light (e.g., u.v. and or near-u.v. wavelengths) and substantially absorptive of another range of wavelengths of light (e.g., ranges of visible wavelengths).

Further, it is desirable to select a colorant that has a high enough solubility in the resin composition to achieve the light absorptive properties without substantially degrading the properties of the polymer and/or substantially interfering with a component (e.g., an enzyme, an enzyme substrate) of the microassay. For example, the resin composition comprising the colorant may absorb about four times as much light in the 480-615 nm range than it absorbs in the 375-450 nm range. Preferably, the resin composition comprising the colorant may absorb more than four times as much light in the 480-615 nm range than it absorbs in the 375-450 nm range.

Thus, there are two factors that can guide the selection of a colorant for use in articles according to the present disclosure: the Absorbance Ratio (A*), which indicates the ability of the resin/colorant mixture to absorb the wavelengths of light used in the detection assay (in this example, wavelengths of about 550 nm and about 600 nm); and the Absorbance fraction (F), which indicates the ability of the resin/colorant mixture to transmit the wavelengths of light used to cure the resin composition (in this example, a wavelength of about 400 nm). Broadly, both A* and F can be calculated for any two substantially non-overlapping ranges of wavelengths. Both factors are defined below with respect to a wavelength (400 nm) that is useful for curing a polymer composition and two wavelengths (550 nm and 600 nm) that fall within a range of wavelengths that are useful to detect a reaction involving the enzyme luciferin:

$$A^* = (A_{550} + A_{600})/2 \text{ where}$$

$A_{550}$=light absorbance at 550 nm, $A_{600}$=light absorbance at 600 nm, and
A=−log(fraction of light transmitted)

$$F = (2 \times A_{400})/(A_{550} + A_{600}) \text{ where}$$

$A_{400}$=light absorbance at 400 nm, $A_{550}$=light absorbance at 550 nm, $A_{600}$=light absorbance at 600 nm, and A=−log (fraction of light transmitted)

A higher A* factor indicates that the resin composition comprising a colorant is absorbing more light in the visible light (550-600 nm in this example) and, therefore, allows less optical cross-talk between adjacent microwells in a microassay. A lower F factor indicates that the resin composition is permitting more near-u.v. light (400 nm in this example) relative to visible light (550-600 nm in this example) and, therefore allows good curing of the polymer while also absorbing light in the longer visible wavelengths.

In some embodiments, the colorant in the monomer mixture provides an Absorbance Ratio (A*) of about 0.3 or greater; preferably, an A* of 0.5 or greater; more preferably an A* of 1.0 or greater; even more preferably an A* of 1.5 or greater, and even more preferably, an A* of 2.0 or greater in a microstructured layer with a thickness of 5 microns. In some embodiments, the colorant in the monomer mixture provides an Absorbance Ratio (A*) of about 0.3 or greater; preferably, an A* of 0.5 or greater; more preferably an A* of 1.0 or greater; even more preferably an A* of 1.5 or greater, and even more preferably, an A* of 2.0 or greater in a microstructured layer with a thickness of 10 microns. The preferred mixtures allow rapid photopolymerization of the resin composition, while keeping the colorant molecularly dispersed in the article after polymerization.

In some embodiments, the colorant in the monomer mixture provides an Absorbance fraction (F) of 0.25 or less, preferably 0.10 or less.

It will be recognized by a person of ordinary skill in the relevant art that the principles embodied by A* and F can be applied to other selected wavelengths for photocuring and the Examples described below are merely exemplary of the way these factors can be used to select combinations of colorants with specific desirable attributes for detecting a luciferase enzyme reaction.

A drawing can illustrate the effects of the length of the optical path between the bottom of a microwell and the image capture device (e.g., a camera or a fiber optic bundle). FIGS. 3A and 3B illustrate several aspects of the disclosed microwell array articles that limit the amount of optical cross-talk according to the present disclosure.

FIG. 3A shows a schematic view of a microwell array article 300a, as shown in FIG. 2A, that is optically coupled to an optical device 390. In this embodiment, the microstructured layer 310 comprises a colorant that is substantially nontransmissive to selected wavelengths of light.

The microwell array article 300a comprises two microwells, 322a and 322b, formed in microstructured layer 310, and an optically-transmissive layer 330. The optical device 390 comprises of an array of sensors 392 (e.g., optical fibers in a fiber optic array or image sensors in a digital camera). Sensors "P" and "Q" represent two individual sensors 392 that are positioned proximate microwells 322a and 322b, respectively. Also shown in FIG. 3A are arrows representing optical signals (e.g., photons) emerging from a biochemical reaction occurring in each respective microwell.

It can be seen in FIG. 3A that light passing into the relatively thicker sidewalls of the microwells does not penetrate far enough through the microstructured layer 310 to be received by any of the sensors 392. This is due to absorption of light by the colorant over the relatively long path length between the microwells 322a and 322b. In contrast, light passing into the relatively thinner path length of the bottom walls of the microwells 322 can be transmitted through the microstructured layer 310 and the optically-transmissive flexible layer 330 and be received by the adjacent sensors 392. In FIG. 3A, only the light transmitted from microwell 322a is received by sensor "P" and only the light transmitted from microwell 322b is received by sensor "Q".

FIG. 3B shows a schematic view of a microwell array article 300b that is optically coupled to an optical device 390. In this embodiment, the microstructured layer 310 comprises a colorant that substantially absorbs selected wavelengths of light and the optically-transmissive layer 330 is relatively thicker than the corresponding layer in FIG. 3A.

The microwell array article 300b comprises two microwells, 322c and 322d, formed in microstructured layer 310, and an optically-transmissive layer 330. The optical device 390 consists of an array of sensors 392 (e.g., optical fibers in a fiber optic array or image sensors in a digital camera). Sensors "R" and "S" represent two individual sensors 392 that are positioned proximate microwells 322c and 322d, respectively. Also shown in FIG. 3B are arrows representing optical signals (e.g., photons) emerging from a biochemical reaction occurring in each respective microwell.

It can be seen in FIG. 3B that light passing into the relatively thicker sidewalls of the microwells does not penetrate far enough through the microstructured layer 310 to be received by any of the sensors 392 due to absorption of light by the colorant over the relatively long path length between the microwells 322c and 322d. In contrast, light passing into the relatively thinner bottom walls of the microwells 322 can be transmitted through the microstructured layer 310 and the optically-transmissive flexible layer 330 and be received by the adjacent sensors 392. In contrast to the microwell array article 300a in FIG. 3A, some light transmitted from microwell 322c is received both by proximate sensor "R" and by distal sensor "S". Similarly, light transmitted from microwell 322d is received both by proximate sensor "S" by distal sensor "R".

Optical cross-talk between adjacent microwells can be minimized by several factors including, for example, an optically nontransmissive colorant dispersed in the microstructured layer, an optically nontransmissive coating on the sidewalls of the microwells, relatively thin bottom walls in the microwells, relatively thin optically-transmissive flexible layers, increasing the spatial separation of the microwells, and any combination of two or more of the foregoing factors. Optical cross-talk can also be affected by the density and cross-sectional area of the individual image sensors, relative to the cross-sectional area of the individual microwells.

As illustrated above, one particular advantage of the present disclosure is that, particularly through the use of thin optically-transmissive layers and fiber optic technology, improved extremely high density microwell arrays can be made.

Assay System:

The present disclosure provides an assay system for detecting an analyte. The assay system comprises a microwell array article as described herein, an optical device, and a processor.

The microwell array article is optically coupled to the optical device. The optical device can be a component of an optical system, as described herein. The optical device or system is capable of obtaining an image of at least one microwell. Preferably, the optical device or system is capable of obtaining simultaneous images of a plurality of microwells. The optical device is capable of providing an image to the processor. In some embodiments, the processor may obtain the image from the optical device.

The processor may comprise a means for storing an image (e.g., memory such as random access memory (RAM), read-only memory (ROM), compact disc read-only memory (CD-ROM), non-volatile random access memory (NVRAM), electrically erasable programmable read-only memory (EEPROM), or flash memory, for example). The processor may further comprise a means for displaying an image (e.g., a monitor). The processor may further comprise image processing and analysis routines to identify, characterize, and/or quantitate an analyte in a microwell. In some embodiments of the present disclosure, detecting the presence or absence of the analyte comprises displaying, analyzing, or printing the image of a microwell.

EMBODIMENTS

Embodiment 1 is an article, comprising
a microstructured layer with upper and lower major surfaces, comprising a plurality of optically-isolated microwells extending between the upper and lower major surfaces; and
an optically-transmissive flexible layer coupled to the lower major surface of the microstructured layer;
wherein each microwell in the microstructured layer comprises a top opening, a bottom opening, and at least one side wall extending between the top opening and the bottom opening;
wherein the optically-transmissive flexible layer has an average thickness of about 2 µm to about 50 µm.

Embodiment 2 is an article, comprising
a microstructured layer with upper and lower major surfaces, comprising a plurality of optically-isolated microwells extending below the upper major surface; and
an optically-transmissive flexible layer coupled to the lower major surface of the microstructured layer;
wherein each microwell in the microstructured layer comprises an opening, an optically-transmissive bottom wall, and at least one side wall extending between the opening and the bottom wall;
wherein the bottom wall has a thickness of about 0.1 µm to about 5 µm.

Embodiment 3 is an article, comprising
a microstructured layer with upper and lower major surfaces, comprising a plurality of optically-isolated microwells extending below the upper major surface; and
an optically-transmissive flexible layer coupled to the lower major surface of the microstructured layer;
wherein each microwell in the microstructured layer comprises an opening, an optically-transmissive bottom wall, and at least one side wall extending between the opening and the bottom wall;
wherein a thickness (t) is defined by a thickness of the bottom wall plus a thickness of the optically-transmissive flexible layer;
wherein t is about 2 µm to about 55 µm.

Embodiment 4 is the article of any one of the preceding embodiments, wherein the microstructured layer comprises a colorant.

Embodiment 5 is the article of embodiment 4, wherein the colorant is selected from the group consisting of carbon black, fuchsin, carbazole violet, and Foron Brilliant Blue.

Embodiment 6 is the article of any one of the preceding embodiments, wherein the optically-transmissive flexible layer is transmissive to a selected wavelength of light.

Embodiment 7 is the article of any one of embodiments 2-6, wherein the bottom wall is substantially transmissive to the selected wavelength of light.

Embodiment 8 is the article of embodiment 6 or embodiment 7, wherein the at least one sidewall is substantially nontransmissive to the selected wavelength of light.

Embodiment 9 is the article of embodiment 8, wherein the at least one sidewall is at least 50% less transmissive of a selected wavelength of light than the bottom wall.

Embodiment 10 is the article of embodiment 8, wherein a sidewall is at least 90% less transmissive of a selected wavelength of light than the bottom wall.

Embodiment 11 is the article of any one of the preceding embodiments, wherein the bottom wall and/or the at least one sidewall of a microwell further comprise a coating.

Embodiment 12 is the article of embodiment 11, wherein the bottom wall and/or the at least one side wall of a microwell further comprises a plurality of coatings.

Embodiment 13 is the article of embodiment 11 or embodiment 12, wherein at least one coating comprises $SiO_2$.

Embodiment 14 is the article of any one of embodiments 11 through 13, wherein at least one coating comprises a reflective coating.

Embodiment 15 is the article of any one of the preceding embodiments, wherein the microstructured layer is a cured polymer derived from a resin.

Embodiment 16 is the article of embodiment 15, wherein the resin is selected from the group consisting of acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof.

Embodiment 17 is the article of embodiment 16, wherein the optically transmissive layer comprises polyethylene terephthalate, polyethylene naphthalate, high density polyethylene, low density polyethylene, or linear low density polyethylene.

Embodiment 18 is the article of embodiment 16 or embodiment 17, wherein the film comprises a multi-layer film.

Embodiment 19 is the article of any one of the preceding embodiments, wherein the optically-transmissive flexible layer further comprises an adhesive.

Embodiment 20 is the article of any one of the preceding embodiments, wherein the microstructured layer further comprises a tab region that is substantially free of microwells.

Embodiment 21 is the article of embodiment 20, wherein the tab region comprises a detachable portion.

Embodiment 22 is the article of any one of the preceding embodiments, further comprising a cover layer coupled to the upper major surface of the microstructured layer.

Embodiment 23 is the article of embodiment 22, wherein the cover layer is removably coupled to the microstructured layer.

Embodiment 24 is the article of any one of the preceding embodiments, further comprising a cover layer coupled to the optically-transmissive flexible layer on a surface opposite the microstructured layer.

Embodiment 25 is the article of embodiment 24, wherein the cover layer is removably coupled to the optically-transmissive flexible layer.

Embodiment 26 is the article of any one of the preceding embodiments, further comprising an optical detection system comprising an optical device, wherein the optical device is optically coupled to a substrate.

Embodiment 27 is the article of embodiment 26, wherein the optical device comprises a fiber optic face plate.

Embodiment 28 is the article of embodiment 26 or embodiment 27, wherein the optical device comprises a CCD image sensor, a CMOS image sensor, or a photomultiplier tube.

Embodiment 29 is the article of any one of embodiments 26-28, wherein the optical system further comprises a processor.

Embodiment 30 is the article of any one of the preceding embodiments, wherein at least one microwell further comprises a polynucleotide.

Embodiment 31 is the article of embodiment 30, wherein the polynucleotide is coupled to a particle.

Embodiment 32 is a process of manufacturing a microwell array article, comprising the steps of:
providing
a tool having a molding surface with a plurality of projections extending therefrom suitable for forming the microstructure elements;
a flowable, curable resin composition;
an optically-transmissive flexible layer having first and second major surfaces;
applying to the molding surface a volume of the flowable curable resin composition suitable for forming desired microstructure elements;
contacting the resin composition with the first major surface of the optically-transmissive flexible layer;
wherein the first major surface of the optically-transmissive flexible layer is surface-treated to promote adhesion to a cured resin composition;
wherein the thickness of the optically-transmissive flexible layer is about 50 μm or less; and
curing the resin composition while in contact with the flexible layer to form a microwell array article comprising a cured microstructured layer including a plurality of microwells bonded to the optically-transmissive flexible layer, and
removing the microwell array article from the tool.

Embodiment 33 is the process of embodiment 32, wherein contacting the resin composition with the first major surface of the optically-transmissive flexible layer comprises applying pressure to the resin composition to substantially displace the resin between the tops of the projections in the tool and the surface of the optically-transmissive layer.

Embodiment 34 is the process of embodiment 32 or embodiment 33, wherein the optically-transmissive flexible layer is surface-treated with a process selected from the group consisting of radiation treatment, corona discharge treatment, flame treatment, plasma treatment, high energy UV treatment, and chemical priming treatment.

Embodiment 35 is the process of any one of embodiments 32 through 34, wherein the optically-transmissive flexible layer is coupled to a carrier.

Embodiment 36 is the process of any one of embodiments 32-35, wherein the resin composition comprises a colorant.

Embodiment 37 is the process of any one of embodiments 34-38, wherein said curing comprises exposing the resin composition to at least one curing treatment selected from the group consisting of actinic radiation from a radiation source, an electron beam, and a chemical curing agent.

Embodiment 38 is the process of any one of embodiments 32-37, wherein the flexible layer has a thickness of about 2 μm to about 48 μm.

Embodiment 39 is the process of any one of embodiments 32-38, further comprising the step of removing a portion of the microstructured layer.

Embodiment 40 is the process of any one of embodiments 32-39, further comprising the step of removing a portion of the optically-transmissive flexible layer.

Embodiment 41 is the process of any one of embodiments 32-40, further comprising the step of disposing a reagent in a microwell.

Embodiment 42 is a method of detecting an analyte in a microwell array, comprising:
providing
a sample suspected of containing an analyte;
a reagent for the optical detection of the analyte;
an optical detection system; and
an article according to any one of embodiments 1-31;
contacting the sample and the reagent in at least one microwells under conditions suitable to detect the analyte, if present, in the at least one microwells; and
using the optical detection system to detect the presence or absence of the analyte in a microwell.

Embodiment 43 is the method of embodiment 42, wherein the optical system is optically coupled to the substrate.

Embodiment 44 is the method of embodiment 42 of embodiment 43, wherein the optical system comprises a fiber optic face plate and wherein using the optical detection system comprises passing a signal through the fiber optic face plate.

Embodiment 45 is the method of any one of embodiments 42-44, wherein the optical system comprises a CCD image sensor, a CMOS image sensor, or a photomultiplier tube.

Embodiment 46 is the method of any one of embodiments 42-45, wherein the optical system further comprises a processor.

Embodiment 47 is the method of any one of embodiments 42-46, wherein detecting the presence or absence of an analyte comprises detecting light that is indicative of the presence of the analyte.

Embodiment 48 is the method of embodiment 47, wherein detecting light comprises detecting light by absorbance, reflectance, or fluorescence.

Embodiment 49 is the method of embodiment 48, wherein detecting light comprises detecting light from a lumigenic reaction.

Embodiment 50 is the method of any one of embodiments 42-48, wherein detecting the presence or absence of the analyte comprises obtaining an image of a microwell.

Embodiment 51 is the method of embodiment 50, wherein detecting the presence or absence of the analyte comprises displaying, analyzing, or printing the image of a microwell.

Embodiment 52 is the method of any one of embodiments 42-51, wherein contacting the sample and the reagent in a plurality of microwells under conditions suitable to detect the analyte comprises an enzyme and an enzyme substrate.

Embodiment 53 is the method of any one of embodiments 42-52, wherein contacting the sample and the reagent in a plurality of microwells under conditions suitable to detect the analyte comprises forming a hybrid between two polynucleotides.

Embodiment 54 is an assay system, comprising:
an article according to any one of embodiments 1-31;
an imaging device optically coupled thereto; and
a processor.

Embodiment 55 is the assay system of embodiment 54, wherein optically coupled comprises adhesively coupling the microwell array article to a solid interface.

Embodiment 56 is a composition, comprising a dye selected from the group consisting of 1-(3-methyl-n-butylamino)-9,10-anthracenedione; 1-(3-methyl-2-butylamino)-9,10-anthracenedione; 1-(2-heptylamino)-9,10-anthracenedione; 1,1,3,3-tetramethylbutyl-9,10-anthracenedione; 1,10-decamethylene-bis-(-1-amino-9,10-anthracenedione); 1,1-dimethyl ethylamino-9,10-anthracenedione; and 1-(n-butoxypropylamino)-9,10-anthracenedione.

Embodiment 57 is the composition of embodiment 56, further comprising a cured polymer derived from a resin.

Embodiment 58 is the composition of embodiment 57, where the cured polymer is derived from a resin selected from the group consisting of acrylate resins, acrylic resins, acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof.

The invention will be further illustrated by reference to the following non-limiting Examples. All parts and percentages are expressed as parts by weight unless otherwise indicated.

EXAMPLES

All parts, percentages, ratios, etc. in the examples are by weight, unless noted otherwise. Solvents and other reagents used were obtained from Sigma-Aldrich Chemical Company; Milwaukee, Wis. unless specified differently.
Materials 3M 8402: a tape obtained from 3M Company, St. Paul, Minn.

3M 8403: a tape obtained from 3M Company, St. Paul, Minn.

Carbon black paste #9B898: 25% carbon black paste obtained from Penn Color, Doylestown, Pa.

Darocur 1173: 2-hydroxy-2-methylprophenone obtained from Ciba Specialty Chemicals, Basel, Switzerland.

Darocur TPO: diphenyl (2,4,6-trimethylbenzoyl) phosphine oxide obtained from Ciba Specialty Chemicals, Basel, Switzerland.

Desmodur W: a diisocyanate, sometimes referred to as H12MDI or HMDI, obtained from Bayer, Pittsburgh, Pa.

Dytek A: an organic diamine obtained from Invista, Wilmington, Del.

EGC-1720: a fluorocarbon solution obtained from 3M Company, St. Paul, Minn.

Fluorescebrite Plain Microspheres: Fluorescent beads obtained from Polysciences, Inc. Warrington Pa.

Irgacure 819: phenyl-bis-(2,4,6-trimethyl benzoyl) phosphine oxide obtained from Ciba Specialty Chemicals, Basel, Switzerland.

Kapton H: a polyimide film obtained from DuPont, Wilmington, Del.

Loparex 10256: a fluorosilicone treated PET release liner obtained from Loparex, Willowbrook, Ill.

Lucirin TPO-L: 2,4,6-trimethylbenzoylphenyl phosphinate obtained from BASF, Luwigshafen, Germany.

Melinex 453: a 25 micron (1 mil) thick polyester film, which is adhesion treated on one side, obtained from Dupont, Wilmington, Del.

Photomer 6210: obtained from Cognis, Monheim, Germany

Photomer 6602: obtained from Cognis, Monheim, Germany

Scotchcast Electrical Resin #5: a resin obtained from 3M Company, St. Paul, Minn.

SilFlu 50MD07: A release liner available from SilicoNature USA, LLC, Chicago, Ill.

SR238: 1,6 hexanediol diacrylate obtained from Sartomer, Inc., Exton Pa.

SR339: 2-phenoxy ethyl acrylate obtained from Sartomer, Inc., Exton Pa.

SR545: an MQ resin obtained from Momentive Performance Materials, Albany, N.Y.

Teonex Q71: a six micron thick poly(ethylene naphthalate), or PEN, film obtained from Dupont-Teijin, Chester, Va.

Vitel 1200B: a copolyester resin obtained from Bostik, Wauwatosa, Wis.

Violet 9S949D: a violet paste containing 20% pigment solids obtained from Penn Color, Doylestown, Pa.
Microreplication Tooling Tooling was prepared by a laser ablation process according to the procedure discussed in U.S. Pat. No. 6,285,001, which is incorporated herein by reference in its entirety. Tool A was constructed by coating a urethane acrylate polymer (Photomer 6602) to an approximately uniform thickness of 165 microns onto an aluminum backing sheet as described in Unites States Patent Application Publication No. 2007/0231541, which is incorporated herein by reference in its entirety, followed by ablating the coating to produce a hexagonally packed array of posts. The resulting posts had a center to center distance of 42 microns. Each post comprised a circular top having a diameter of 27 microns, a sidewall angle of approximately 10 degrees, and a height of 39 microns. Tool B was constructed by ablating a 125 micron thick Kapton H polyimide film to construct posts having a hexagonally packed array of posts. The resulting posts had a center to center distance of 34 microns and each post comprised a circular top having a diameter of 27 microns, a sidewall angle of approximately 10 degrees, and a height of 34 microns. Tool C was constructed from Photomer 6602 in the same way as Tool A to make a hexagonally packed array of posts with center to center distance of 34 microns. Each post comprised a circular top having a diameter of 27 microns, a sidewall angle of approximately 10 degrees, and a height of 34 microns.
Tooling Surface Treatments The polymer Tool A was first plasma treated using an apparatus described in detail in U.S. Pat. No. 5,888,594, which is incorporated herein by reference in its entirety. The polymer tool was mounted onto the cylindrical drum electrode and the chamber was pumped down to a base pressure of $5 \times 10^{-4}$ Torr. Argon gas was introduced into the chamber at a flow rate of 500 sccm (standard cubic centimeters per minute) and plasma ignited and maintained at a power of 500 watts for 30 seconds. After the argon plasma treatment, tetramethylsilane vapor was introduced into the chamber at a flow rate of 360 sccm and the plasma sustained at a power of 500 watts for 30 seconds. After the plasma treatment in tetramethylsilane vapor, oxygen gas was introduced into the chamber at a flow rate of 500 sccm and plasma sustained at a power of 500 watts for 60 seconds. The pressure in the chamber during these plasma treatment steps was in the 5-10 mTorr range. The plasma chamber was then vented to atmosphere and the treated tool was dipped in EGC-1720 fluorocarbon solution. The treated tool was heated in an oven at 120 C for 15 minutes. Tool C was treated in the same way as Tool A.

The polymer Tool B was plasma treated using an apparatus described in detail in U.S. Pat. No. 5,888,594, which is incorporated herein by reference in its entirety. The polymer tool was mounted onto the cylindrical drum electrode and the chamber was pumped down to a base pressure of $5 \times 10^{-4}$ Torr. Argon gas was introduced into the chamber at a flow rate of 500 sccm and plasma ignited and maintained at a power of 500 watts for 30 seconds. After the argon plasma treatment, tetramethylsilane vapor was introduced into the chamber at a flow rate of 360 sccm and the plasma sustained at a power of 500 watts for 30 seconds.

Resin Preparation

Resin formulations were prepared as follows.

Solution A: 1125 grams of Photomer 6210, 375 grams of SR238 and 15 grams of Darocur 1173 were combined in a glass jar. Solution B: 3.75 g of Irgacure 819 was added to SR339 followed by roller mixing overnight to dissolve the Irgacure 819. Solution C: 3.75 grams of Irgacure 819 was added to 187.5 grams of SR 238 followed by roller mixing 18 hours to dissolve the Irgacure 819. Solution D: solutions A, B, and C were combined in a glass jar followed by mixing. To this was added Darocur 1173 (3.7 g) and Darocur TPO (32 g) followed by roller mixing for 30 minutes.

Solution E: Solution D (708 g) was placed in an amber glass jar. Carbon black paste #9B898 (97 g) was added to the solution and roller mixed for 18 hours to provide a resin formulation with a final carbon black concentration of 3%.

Solution F: Solution D (466 g) was placed in an amber glass jar. Carbon black paste #9B898 (40.5 g) was added to the solution and roller mixed for 18 hours to provide a resin formulation with a final carbon black concentration of 2%.

Solution G: Solution D (466 g) was placed in an amber glass jar. Carbon black paste #9B898 (19.4 g) was added to the solution and roller mixed for 18 hours to provide a resin formulation with a final carbon black concentration of 1%.

Solution H: Solution D (708 g) was placed in an amber glass jar. Violet 9S949D (121 g) was added to the solution and roller mixed for 18 hours to provide a resin formulation with a final violet pigment concentration of 3%.

Solution I: Into a 500 mL glass jar was placed 99.00 g of SR238 (1,6 hexanediol diacrylate) and 10.00 g of SR339. To the solution was added 5.94 g of oil blue A (solvent blue 36) and 5.94 g of solvent violet 37 and the composition was mixed to disperse/dissolve the dyes. The mixture was centrifuges and the supernatant (193.85 g) was recovered. 0.68 g of Irgacure 819 and 3.30 g of TPO-L was added to the supernatant. The jar was then capped and placed in a shaker for mixing overnight. Most of the dye appeared to be dissolved in the acrylates. Subsequently, to the solution was added 90.00 g of the base resin with Photomer 6210. The solution was subjected to a further mixing in a shaker for 1 hour. A homogeneous blue-colored solution was obtained.

Examples 1-5

Microreplication was performed using a UV curing process as described in PCT Publication No. WO 9511464, and described above. Unless noted otherwise, the UV cure process used in these examples did not include the optional second radiation source described in FIG. 5.

Tool A, having a patterned area of approximately 7 inches by 36 inches, was secured to a mandrel having an approximate diameter of 37 inches using 3M 8402 adhesive tape. The Melinex 453 film was threaded from the unwind idler, along the surface of the Tool A, to the rewind idler as shown in FIG. 5. The surface-treated (adhesion-promoting) side of the film was facing the tool. The mandrel was heated to 54 C (130 F). The film was run at a line speed of 10 cm/s (20 feet per minute) at a nip pressure of 207 kPa (30 psi) at the contact point of the first nip roller (a 95 Shore D nitrile rubber roller) and the mandrel. Resin was applied to the film by manually pouring a small continuous bead of resin solution on the film at the hopper location upstream from the mandrel as depicted in FIG. 5. The resin spread laterally across the width of the tool at the rubber nip roller, forming a bank of solution approximately 9 inches wide. Resin solutions E, F, and G were used in Examples 1, 2, and 3, respectively. Resins were cured using radiation from Fusion D lamps. The Fusion D lamps were operated at an input power of 236 watts per cm. The cured microwell array film article was removed from the tool at the second nip roller and wound on the rewind idler as shown in FIG. 5. Additional samples were made with the above procedure using Tool B instead of Tool A. Example 4 was made by using Tool B with resin solution F and Example 5 was made by using Tool B with resin solution H.

Cure depth for several examples were determined using a combination of SEM imaging and a thickness gauge and are shown in TABLE 1. It can be seen from these examples that increased photoinitiated cure depth can be accomplished by providing a tooling material that allows greater penetration of light (example 1) or alternatively adding a wavelength specific colorant with a lower absorbance cross section in the wavelength range of the photoinitiator (Example 5).

TABLE 1

Cure Depth

| Example Number | Resin Solution | Tool | Microstructure Cure Depth (microns) |
|---|---|---|---|
| 1 | F (3% carbon black) | A (urethane acrylate) | 39 (full cure depth) |
| 4 | F (2% carbon black) | B (polyimide) | about 12 |
| 5 | H (3% violet pigment) | B (polyimide) | 34 (full cure depth) |

Portions of selected samples were cut and dip coated using Scotchcast Electrical Resin #5. The samples were allowed to cure for at least 24 hours before microtoming. The embedded samples were thin sectioned (10-um sections) using a diamond knife. The sections were placed in 1.515 RI oil and covered with a cover slip prior to imaging. Samples were imaged by optical microscopy. A number of sections (listed as "Count" in TABLE 2) were measured to determine the average thickness of the well base (bottom wall), as shown in TABLE 2.

TABLE 2

Thickness of material at the base of the wells in microns

|  | Example 3 1% carbon (G) | Example 2 2% carbon (F) | Example 1 3% carbon (E) |
|---|---|---|---|
| Average | 0.9 | 2.2 | 1.8 |
| Std. Dev. | 0.3 | 0.6 | 0.4 |
| CV | 0.31 | 0.27 | 0.22 |
| Minimum | 0.4 | 1.1 | 1.2 |
| Maximum | 1.4 | 3.5 | 3.0 |
| Count | 18 | 24 | 22 |

Figure 6A:
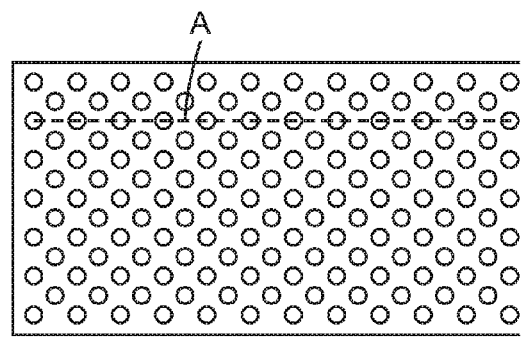
FIG. 6a is a schematic top view of a microwell array article, showing the line along which an image of the microwell array article was analyzed.
Figure 6B:
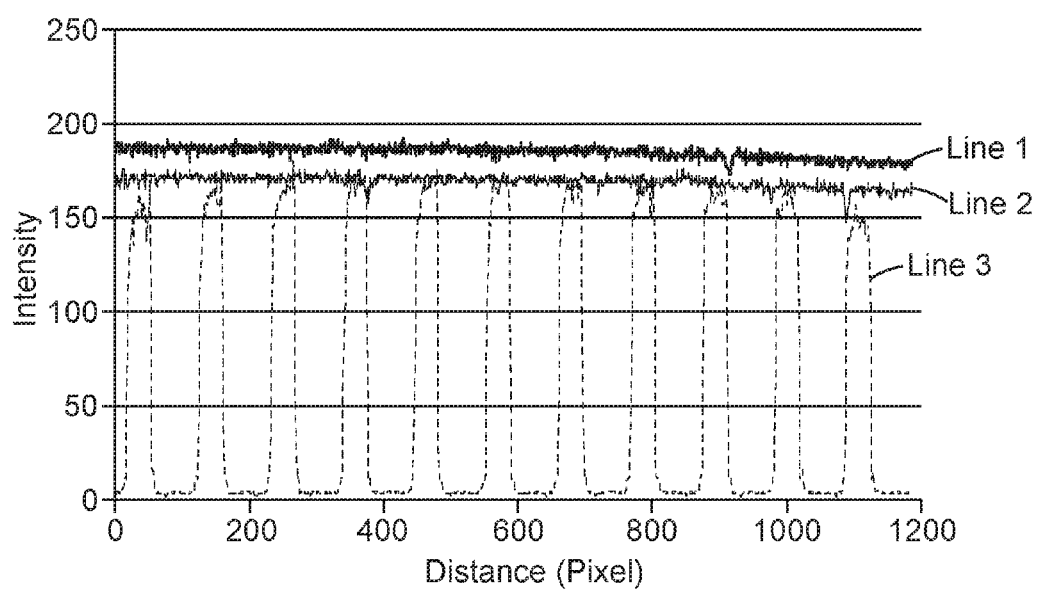

Approximately 1×1 inch samples were obtained from microstructured film examples 1-3 and Melinex 453 film. The films were placed on a 1×3 inch microscope slide, with a small gap (no film) between the samples. Brightfield transmission images were obtained using a Zeiss AxioPlan 2 microscope (Plan-Neofluor 10×/0.03 objective) and a Zeiss AxioPlan 2 digital camera (8 bit). Prior to final image acquisition the light intensity was adjusted to ensure the blank area between the films was below the saturation level of the digital camera. Line scans of each image were produced using ImagePro Plus image analysis software (Media Cybernetics) across the "blank" area of the slide (the gap between the films), an area of the slide that contained just the Melinex 453 film, and an area of the slide that contained the composite article comprising the colorant-containing resin cured on the Melinex 453 substrate. FIG. 6A is a drawing of a top view of one of the composite articles of Example 1, with the path of a linescan shown as dashed line A across the circular microwells and the area between the microwells. FIG. 6B (line 3) shows the pixel intensities of each pixel along the line scan shown in FIG. 6A. Also shown in FIG. 6B are the corresponding line scans for the "blank" (no film, line 1) and PET film (film only, line 2) images. Pixel intensities from the well bottoms were compared to the pixel intensities of the PET film to estimate the average percent transmission of light through the bottom walls of the wells. The calculated results are reported in TABLE 3. It can be observed from these measurements that the thin well base substantially transmits light while the walls are substantially non-transmissive.

TABLE 3

Light transmission through well base

| Example Number | % transmission |
| --- | --- |
| 3 (1% carbon black) | 86.9 |
| 2 (2% carbon black) | 87.9 |
| 1 (3% carbon black) | 80.2 |

Lateral light transmission through the sidewalls in the X-Y plane (see FIG. 1) of Example 1 was estimated by preparing a cured film of uniform thickness similar to the midpoint sidewall thickness in Example 1 (approximately 5 microns). A small amount of solution E was applied to a polyester film 1. This was covered with a second film 2 and manual pressure was applied to spread solution E between the films. The solution between the films was cured by passing under a UV source (500 W fusion lamp) at 7.6 cm/s (15 ft/min) with film 1 facing the UV source. Film 2 was removed and the resin adhered to film 1 on the UV-exposed side was washed to remove uncured monomer. Cured resin thickness was measured using a caliper gauge. The mean thickness was determined to be 4 microns. A portion of the film containing the cured resin was placed in a spectrophotomer (Tecan Infinite M200). Light transmission at 550 nanometers was measured at three locations. For the 4 micron film, a mean absorbance value of 1.4 was obtained, corresponding to a light transmission of 4%. This example serves to illustrate that the microstructured wells are substantially transmissive along the Z axis and substantially nontransmissive in the X-Y plane.

Examples 6 and 7

Six micron thick Teonex Q71 film was primed on one side with a 5% solids solution of Vitel 1200B in an 85%/15% mixture of dioxolane and cyclohexanone via a slot-die coater, followed by drying in an oven at 160° F. for 2 minutes. The thickness of the coating was 300 nanometers as measured with a white light interferometer. The film was then coated on the opposite side with a silicone-polyurea adhesive which consisted of a 28% solids solution of an MQ resin (SR545) and a silicone polyurea (SPU) elastomer at a ratio of 55:45. The SPU elastomer was formed through the condensation reaction of a 33 kDa diamino terminated polydimethylsiloxane, Dytek A, and Desmodur W in a ratio of 1:1:2, as described in U.S. Pat. No. 6,824,820. The film was then dried in an oven at 160° F. for 2 minutes and laminated to a PET film by passing the material through a nip roll in contact with Loparex 10256 fluorosilicone treated PET release liner. The thickness of the coating was 4.2 microns as measured by a white light interferometer.

Example 6 was made by performing microreplication as in Examples 1-5 using the coated Teonex Q71 film in place of the Melinex 453 polyester film and by using Tool C and resin solution H. Example 7 was made as Example 6 except that resin solution I was used. In Examples 6 and 7 the Vitel 1200B-treated side of the Teonex Q71 film was positioned to face toward the replication tool.

Figure 7:
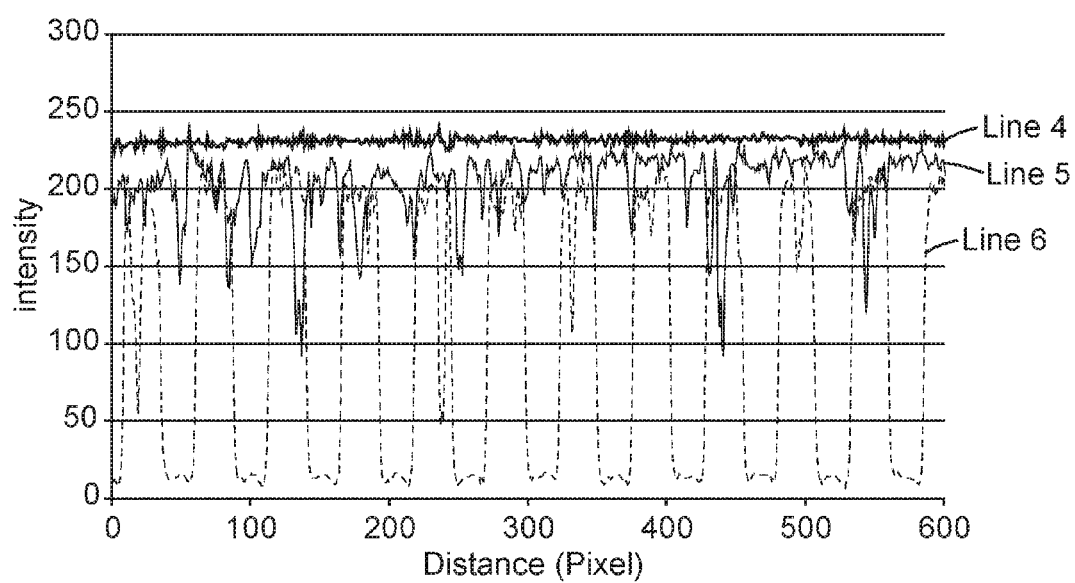
FIG. 7 is a graph of the pixel intensities from the image of another microwell array.

Light transmission through the well base of the microstructure of Example 6 was measured as described for Examples 1-3 above. FIG. 7 shows the results of line scans through a "blank" portion of a slide (line 4), through the adhesive-coated PEN film (line 5), and through the microwell array article (line 6), respectively.

Example 8

A sample made according to Example 1 was coated with a layer of silicon dioxide as follows to produce Example 8. The silica deposition was done in a batch reactive ion plasma etcher (Plasmatherm, Model 3280). The microreplicated article was placed on the powered electrode and the chamber pumped down to a base pressure of 5 mTorr. The article was plasma treated first in an argon plasma at 25 mTorr pressure for 20 seconds. Following this, tetramethylsilane vapor was introduced at a flow rate of 150 sccm and plasma maintained at a power of 1000 watts for 10 seconds, following which, oxygen gas was added to the tetramethylsilane at a flow rate of 500 sccm with the power maintained at 1000 watts for another 10 seconds. After this step, the tetramethylsilane vapor flow rate was decreased in a stepwise manner from 150 sccm to 50 sccm, 25 sccm and 10 sccm while the plasma was still on and each of these steps lasted for 10 seconds. After the last step of tetramethylsilane vapor flow of 25 sccm, the flow was disabled and a 2% mixture of silane gas in argon was introduced instead at a flow rate of 1000 sccm with the plasma maintained at 1000 watts and treatment performed for another 60 seconds. The plasma chamber was subsequently vented to atmosphere and the plasma treated microreplicated article was removed from the chamber.

Examples 9 and 10

Microwell array articles were prepared by casting and curing solution E onto a 25 micron (1 mil) PET film as in Example 1. The PET side was exposed to a solution of potassium hydroxide (40%) containing ethanolamine (20%) to chemically etch the PET film. Etching was accomplished placing the microstructured side of a section of film (about 7.6 cm (3 inches) by 10 cm (4 inches)) against a sheet of printed circuit board material. The perimeter of the film was sealed against the board using 3M 8403 tape to prevent exposure of the solution to the structured side. The potassium hydroxide/ethanolamine solution was placed in a large glass container and heated to 80 C using a water bath. The boards with adhered films were immersed in the bath for a specified time followed by washing with water. Films etched for 3 minutes had 12 microns of remaining PET (Example 9). Films etched for 6 minutes and 10 seconds had 5 microns of PET remaining (Example 10).

Examples 11-14

A silicone adhesive was coated onto a liner at various thicknesses. The adhesive consisted of a 28% solids solution of an MQ resin (SR545) and a silicone polyurea (SPU)

elastomer at a ratio of 55:45. The SPU elastomer was formed through the condensation reaction of a 33 kDa diamino terminated polydimethylsiloxane, Dytek A, and Desmodur W in a ratio of 1:1:2, as in U.S. Pat. No. 6,824,820. The liner used was SilFlu 50MD07 which uses a fluorosilicone release chemistry on clear, 50 micron (2 mil) PET. The adhesive was coated using a knife coater with a 50 micron (2 mil) wet gap. The adhesive was diluted with toluene to achieve various thicknesses. The coated liner was dried in an oven at 115° C. for six minutes.

The adhesives were then laminated to samples of microwell array articles formed on PET film according to Examples 8, 15 and 16 using a rubber roller. The well structures were protected from damage with a PET film, which was then discarded. Example 11 was made by laminating 39 micron thick adhesive to the microwell array of Example 1, which had a PET film thickness of 25 microns, for a total base thickness of 64 microns. Example 12 was made by laminating 7 micron thick adhesive to the microstructure of Example 1, which had a PET film thickness of 25 microns, for a total base thickness of 32 microns. Example 13 was made by laminating 3 micron thick adhesive to the microstructure of Example 9, which had a PET film thickness of 12 microns, for a total base thickness of 25 microns. Example 14 was made by laminating 2 micron thick adhesive to the microstructure of Example 10, which had a PET film thickness of 5 microns, for a total base thickness of 7 microns.

To simulate an optical assay coupled to a detection device via a fiber optic face plate, light spread was measured as function of total base thickness below the microstructure (i.e., the base thickness included both the PET film plus the adhesive layer). After etching and application of adhesive, sections of films were applied to a fiber optic face plate (6 micron fiber diameters, 47 A glass, Schott North America). Approximately 20 µl of aqueous solution containing approximately 1000 fluorescent beads (27 micron Fluorescebrite Plain Microspheres) was placed on the microstructured side of the laminated film. Beads were allowed to settle into the base of the microstructured wells by gravity. After the water was allowed to evaporate the laminated film/face plate assembly was placed in a fluorescence microscope (Zeiss AxioPlan 2 microscope, Plan-Neofluor 10×/0.03 objective, with fluorescein filter set) with the microstructure side facing down (away from the objective). The microscope was focused on the back side of the face plate. Images of the back side of the faceplate were acquired using a fluorescein filter set. The degree of light spread was approximated by counting the number of 6 micron fibers across the diameter of the fluorescent areas projected on the face plate. The results are shown in TABLE 4. It can be seen from this data that minimization of the base layer thickness decreases the amount of lateral light spread, which in turn minimizes optical cross talk between neighboring wells.

TABLE 4

Approximate projected diameter of 27 micron beads

| Example Number | Base Thickness (PET + adhesive) (microns) | Number of 6 micron fibers across diameter of projected bead image | Approximate Projected diameter of 27 micron bead on faceplate (microns) |
|---|---|---|---|
| 11 | 64 | 11 | 66 |
| 12 | 32 | 8 | 48 |
| 13 | 15 | 6 | 36 |
| 14 | 7 | 5 | 30 |

Examples 15-72

Test for Absorbance fraction (F) of a dye: A double-beam spectrometer operative from 350 nm to 750 nm, furnished with 10.00 mm cells and spectrophotometric grade ethyl acetate was used in these Examples. The reference cell contained ethyl acetate. A very small amount of a dye, dissolved in ethyl acetate, and providing a peak absorbance between 0.5 and 2.0 was placed in the sample cell. The absorbance was measured at 400 nm, 550 nm, and 600 nm. The F fraction was calculated as $2 \times A_{400}/(A_{550}+A_{600})$. This ratio is a strong indicator of useful transmittance in the 375-450 nm region.

Test for coloration of a monomer mixture comprising a colorant: The monomer mixture (50 wt % 1,6-hexanediol diacrylate containing 0.1% TPO photosensitizer+50 wt % 6210 photomer) was combined with 1 to 5 wt % of each dye in a closed vessel with good mechanical mixing (as by rolling or end-to-end inversion). Mixing was done for 24-72 hours. The mixing vessel was subjected to centrifugation to settle undissolved material. Without separation from the pellet (if present), 1% or less of the supernatant was withdrawn and diluted 1:1000 in ethyl acetate or monomer mixture (as indicated in Table 5). The A* ratio and F ratio were calculated as described above and are shown in Tables 5 and 6.

Table 5 shows the pertinent data for a wide variety of dyes having absorptions in the 500-650 nm range. The commercially-available dyes are listed according to the generic names listed in the Color Index published by the Society of Dyers and Colourists and the American Association of Textile Chemists and Colorists. Anthraquinone 9,10-anthracenedione) dyes are designated "Q". Non-anthraquinone dyes are typically classified as "azo dyes" or the like in the Colour Index.

TABLE 5

Commercially-available dyes absorbing in the 500-650 nm region. The listed dyes are soluble in ethyl acetate (E) and/or in the monomer mixture (H).

| Example | Generic Name | Spectral solvent | Lambda max (nm) | Lambda #2 (nm) | Range, nm 50% max | Anthraquinone | A* | F |
|---|---|---|---|---|---|---|---|---|
| 15 | Solvent Blue 16 | E | 641 | 594 | 554-659 | Q | .61 | .12 |
| 16 | Solvent Blue 30 | E | 625 | 590 | 544-658 | Q | .63 | .24 |
| 17 | Solvent Blue 36 | E | 639 | 594 | 566-656 | Q | .58 | .09 |
| 18 | Solvent Blue 74 | E | 643 | 595 | 560-660 | Q | .53 | .17 |
| 19 | Solvent Blue 98 | E | 646 | 597 | 569-663 | Q | .52 | .18 |
| 20 | Solvent Blue 102 | E | 641 | 594 | 563-658 | Q | .50 | .12 |

TABLE 5-continued

Commercially-available dyes absorbing in the 500-650 nm region. The listed
dyes are soluble in ethyl acetate (E) and/or in the monomer mixture (H).

| Example | Generic Name | Spectral solvent | Lambda max (nm) | Lambda #2 (nm) | Range, nm 50% max | Anthraquinone | A* | F |
|---|---|---|---|---|---|---|---|---|
| 21 | Solvent Violet 11 | E | 544 | 583 | 498-600 | Q | .63 | .05 |
| 22 | Solvent Violet 13 | E | 584 | 560 | 510-631 | Q | .82 | .17 |
| 23 | Solvent Violet 14 | E | 535 | — | 472-586 | Q | .62 | .11 |
| 24 | Solvent Violet 16 | E | 560 | 614 | 524-630 | Q | .71 | .09 |
| 25 | Solvent Violet 37 | H | 591 | 551 | 510-611 | Q | .49 | .07 |
| 26 | Disperse Blue 354 | E | 602 | — | 553-638 | | .79 | .05 |
| 27 | Disperse Violet 5 | H | 541 | — | 484-584 | | .50 | .42 |
| 28 | Disperse Violet 10 | H | 511 | — | 450-564 | | .50 | .24 |
| 29 | Disperse Violet 11 | H | 545 | 583 | 499-600 | Q | .48 | .04 |
| 30 | Disperse Violet 17 | H | 520 | — | 475-571 | | .08 | .15 |
| 31 | Disperse Violet 26* | H | 539 | 577 | 494-594 | Q | .33 | .05 |
| 32 | Disperse Violet 27 | H | 550 | 582 | 503-620 | Q | .28 | .12 |
| 33 | Disperse Violet 28 | H | 550 | 585 | 504-606 | Q | .08 | .02 |
| 34 | Disperse Violet 29 | H | 550 | 588 | 501-608 | Q | .67 | .04 |
| 35 | Disperse Violet 31* | E | 534 | 577 | 495-594 | Q | .36 | .03 |
| 36 | Disperse Violet 33 | E | 512 | — | 449-565 | | .25 | .20 |
| 37 | Disperse Violet 36 | H | 530 | 570 | 491-584 | Q | .04 | .22 |
| 38 | Disperse Violet 40 | H | 507 | — | 445-563 | | .23 | .28 |
| 39 | Disperse Violet 42 | H | 517 | — | 459-562 | | .07 | .22 |
| 40 | Disperse Violet 44 | H | 540 | 580 | 490-600 | Q | .07 | .10 |
| 41 | Disperse Violet 50 | H | 538 | — | 482-579 | | .16 | .29 |
| 42 | Disperse Violet 52 | H | 527 | — | 466-570 | | .17 | .14 |
| 43 | Disperse Violet 63 | H | 545 | — | 493-585 | | .60 | .07 |
| 44 | Disperse Violet 64 | E | 527 | — | 469-580 | | .06 | .10 |
| 45 | Solvent Red 19 | E | 532 | — | 473-571 | | .25 | .44 |
| 46 | Solvent Red 24 | E | 511 | — | 452-557 | | .29 | 1.00 |
| 47 | Solvent Red 27 | E | 511 | — | 447-559 | | .42 | 1.11 |
| 48 | Solvent Red 91 | E | 559 | — | 458-584 | | .25 | .71 |
| 49 | Solvent Red 127 | E | 520 | 553 | 494-574 | Q | .45 | .16 |
| 50 | Solvent Red 166 | E | 537 | — | 465-584 | | .33 | 1.07 |
| 51 | Solvent Red 172 | E | 528 | 565 | 480-582 | Q | .27 | .09 |
| 52 | Disperse Red 5 | E | 507 | — | 443-563 | | .22 | .30 |
| 53 | Disperse Red 8 | E | 519 | — | 457-568 | | .26 | .19 |
| 54 | Disperse Red 9 | E | 498 | — | 448-543 | | .33 | .44 |
| 55 | Disperse Red 10 | E | 480 | — | 418-537 | | .23 | 1.79 |
| 56 | Disperse Red 11 | E | 529 | 566 | 484-582 | Q | .18 | .05 |
| 57 | Disperse Red 13 | E | 499 | — | 438-552 | | .16 | .47 |
| 58 | Disperse Red 15 | E | 525 | 560 | 476-576 | Q | .47 | .06 |
| 59 | Disperse Red 21 | E | 500 | — | 438-556 | | .25 | .46 |
| 60 | Disperse Red 24 | E | 503 | — | 441-559 | | .23 | .32 |
| 61 | Disperse Red 27 | E | 518 | — | 459-560 | | .13 | .18 |
| 62 | Disperse Red 30 | E | 446 | — | 436-551 | | .10 | .54 |

TABLE 6

List of other dyes absorbing in the 500-650 nm region. The listed dyes are soluble in ethyl acetate (E) and/or in the monomer mixture (H). The dyes classes are anthraquinone dyes (Q), bis(trifluoromethanesulfonyl)methylene merocyanine dyes (S), p-(tricyanovinyl) arylamine dyes (V), merocyanine dyes (M), and indoaniline (indophenol) dyes (I), respectively.

| Example | Chemical Abstract Service Name | CAS No. | Spectral solvent | Lambda max (nm) | Lambda #2 (nm) | Range, nm 50% max | Dye Class | A* | F |
|---|---|---|---|---|---|---|---|---|---|
| 63 | 4-[4,4-bis[(trifluoromethyl)sulfonyl]-1,3-butadien-1-yl]-Benzenamine | 58559-02-7 | E | 533 | — | 504-537 | S | .47 | .004 |
| 64 | 4,4'-[4,4-bis[(trifluoromethyl)sulfonyl]-1,3-butadienylidene]bis[N,N-dimethyl-Benzenamine | 149679-67-4 | E | 531 | — | 499-569 | S | .26 | .004 |
| 65 | 4-[4-[4,4-bis[(trifluoromethyl)sulfonyl]-1,3-butadien-1-Morpholine | 126942-09-4 | E | 529 | — | 492-554 | S | .75 | .03 |
| 66 | 2-[4-(dibutylamino)phenyl]-1,1,2-Ethenetricarbonitrile | 63504-26-7 | E | 517 | — | 474-547 | V | .34 | .003 |
| 67 | 1,5-bis[(1-methylethyl)amino)]-9,10-Anthracenedione | 33175-76-7 | E | 509 | — | 457-556 | Q | .32 | .26 |

TABLE 6-continued

List of other dyes absorbing in the 500-650 nm region. The listed dyes are soluble in ethyl acetate (E) and/or in the monomer mixture (H). The dyes classes are anthraquinone dyes (Q), bis(trifluoromethanesulfonyl)methylene merocyanine dyes (S), p-(tricyanovinyl) arylamine dyes (V), merocyanine dyes (M), and indoaniline (indophenol) dyes (I), respectively.

| Example | Chemical Abstract Service Name | CAS No. | Spectral solvent | Lambda max (nm) | Lambda #2 (nm) | Range, nm 50% max | Dye Class | A* | F |
|---|---|---|---|---|---|---|---|---|---|
| 68 | 2-[(1-methyl-4(1H)-quinolinylidene)methyl]-5-nitro-Benzonitrile | 63945-43-7 | E | 553 | — | 493-597 | M | .36 | .10 |
| 69 | 4-[[4-(dimethylamino)phenyl]imino]-1(4H)-Naphthalenone | 132-31-0 | E | 598 | — | 489-671 | I | .55 | .33 |
| 70 | 4-[[4-(diethylamino)phenyl]imino]-1(4H)-Naphthalenone | 2363-99-7 | E | 580 | — | 503-626 | I | .36 | .16 |
| 71 | 1-(hexylamino)-4-hydroxy-9,10-Anthracenedione | 63768-04-7 | H | 557 | 596 | 503-617 | Q | 2.38 | .14 |
| 72 | Intratherm Brilliant Blue 308 (available from Crompton Corporation, Middlebury, CT) | | E | 582 | — | 474-660 | | .78 | .30 |

Example 73

Preparation of 1-n-hexylamino-4-hydroxy-9,10-anthracenedione

The reaction was run on a magnetic-stirring hot plate in a 125 mL Erlenmeyer flask fitted with a reflux condenser and with a PTFE-coated magnetic stirring bar. In it was placed Quinizarin, 6.06 g. (25 mmol), potassium carbonate 0.11 g. (0.8 mmol), manganous chloride tetrahydrate catalyst 0.44 g (2.2 mmol), and to this was added 75 g. 1-methoxy-2-propanol, b.p. 119 C, containing 5.06 g. n-hexylamine (50 mmol). The reaction mixture was heated to reflux with magnetic stirring for 6 hours. Then dilution with water precipitated the dye product which, after decantation of the liquid, steeping in hot water, and drying, weighed 7.39 g. From this, 5.48 g. was placed in a filter thimble in a Jacketed Soxhlet Extractor, and in the 250 mL boiling flask was placed n-pentane. Heating caused cycling every 5 minutes for 68 hours (over 750 cycles). The boiling flask contained a dark bluish solution of 1,4-bis(hexylamino)-9,10-anthracenedione and some of the desired product. The solution was decanted off a dark crystalline solid product, which was washed once with pentane and dried (weight 2.88 g. indicating 52% yield) The solid had a capillary melting point 77 to 79 C, indicating good purity. The compound was tested for Absorbance fraction (F) and coloration (A*) as described for Examples 15-43 and the results are reported in Table 7.

Example 74

Preparation of 1-(3-methylbutylamino)-4-hydroxy-9,10-anthracenedione

In a 125 mL Erlenmeyer flask modified with a sampling port was placed Quinizarin, 6.06 g (25 mmol); NaBH$_4$, 38 mg (1.0 mmol); 3-methylbutylamine, 2.18 g (25 mmol); piperidine, 2.13 g (25 mmol); and 1-methoxy-2-propanol, 60 g, and the reaction was run as in Example 1. It was sampled at 0.5, 0.75, and at the 3.0 hr termination. The samples were subjected to TLC using toluene as the eluent. Quinizarin (0.64 R$_f$) was observed only in the 0.5 hr sample. The desired product (0.57 R$_f$) appeared fully formed at 0.75 hr. The reaction mixture was drowned in 700 mL hot water containing 2.50 g (25 mmol) conc. HCl to neutralize the piperidine. Secondary amines appear unreactive in substitution on Quinizarin. The precipitated dye product, after coagulation by concentration, was steeped twice in 900 mL portions of hot water. The dried crude oily product was chilled to enable shattering the product and transferring it to a filter thimble, where it was distributed between layers of cotton to minimize aggregation. Extraction by petroleum ether in the Jacketed Soxhlet apparatus was run for 200 cycles, the boiler was cooled, and the dark purple solution was decanted off. The crystallized solid product was washed with petroleum ether and dried. (weight 3.84 g, indicating 50% yield), The capillary melting point of the product was 86-89 C. The compound was tested for Absorbance fraction (F) and coloration (A*) as described for Examples 15-43 and the results are reported in Table 7.

Example 75

Alternative preparation of 1-(3-methylbutylamino)-4-hydroxy-9,10-anthracenedione 1-(3-methylbutylamino)-9,10-anthracenedione was also prepared by an alternative procedure without the use of NaBH$_4$ catalyst. In this alternative procedure, the procedure of Example 74 was followed with these changes; no NaBH$_4$, and to remove possible weakly catalytic reagents, 1,2-diethoxyethane of similar b.p. to replace 1-methoxy-2-propanol, and 1-methylmorpholine (25 mmol) to replace piperidine. The reaction was sampled at 2, 18, 24, 48, and at the 70 hr termination, at which time the TLC showed no Quinizarin. This showed that the NaBH4 accelerated the reaction as much as 100-fold. The desired reaction product (55% yield) was recovered as in Example 74. The capillary melting point was 86-87 C.

Example 76

Preparation of 1-(3-methoxypropylamino)-4-hydroxy-9,10-anthracenedione

The procedure of Example 74 was followed, but with replacement of 3-methylbutylamine by 3-methoxypropylamine, 2.23 g (25 mmol), and of the piperidine by 1-methylmorpholine (25 mmol). The reaction was set to run on a timer for 15 hr without sampling. When drowned in 700 mL water a crystalline precipitate formed. After steeping as in Example 74 and drying, followed by Jacketed Soxhlet extraction with petroleum ether for 1100 cycles, the crystalline solid product was recovered (weight 5.23 g, 67% yield). The capillary melting point was 120-121 C. The compound was tested for Absorbance fraction (F) and coloration (A*) as described for Examples 15-43 and the results are reported in Table 7.

Example 77

Preparation of 1-(n-butoxypropylamino)-4-hydroxy-9,10-anthracenedione

By the procedure of Example 74 but in a similar 50 mL Erlenmeyer flask was placed Quinizarin, 2.43 g (10 mmol); NaBH4, 30 mg (0.8 mmol); 3-(n-butoxy)propylamine, 1.31 g (10 mmol); morpholine, 0.87 g (10 mmol); 1,4-dioxane, 18 g: and (2-methoxyethyl) ether, 6 g. The mixture was refluxed with magnetic stirring. Samples for TLC were taken at 1, 2, 4, and 6 hr (termination) as in Example 74 except that dibutyl ether (99%) was used as the eluent. The purple product had an $R_f$ of 0.52. Only a trace of Quinizarin ($R_f$ of 0.84) was observed in the 6 hr sample. Drowning, steeping, drying, and Jacketed Soxhlet extraction with pentane as in Example 2 gave the desired product in solution which, upon drying, resulted in an oil product (2.17 g, 61% yield) which later crystallized to a waxy solid having capillary melting point 46-50 C, and DSC melting point 48 C as shown in Table IV. The compound was tested for Absorbance fraction (F) and coloration (A*) as described for Examples 15-43 and the results are reported in Table 7.

Example 78

Preparation of 1-(2-ethylhexylamino)-4-hydroxy-9, 10-anthracenedione

The procedure of Example 74 was followed, but with replacement of the amines by 2-ethylhexylamine, 3.23 g (25 mmol) and morpholine, 2.18 g (25 mmol), and of the 1-methoxy-2-propanol by 1,2-diethoxyethane, 60 g. The NaBH4 was solubilized by 15-Crown-5, 0.26 g (1.18 mmol). TLC samples were taken at 1, 2, 4, and 8 hr (termination). As in Example 74 the reaction mix was drowned, steeped, and dried (8.21 g) and subjected to Jacketed Soxhlet extraction with petroleum ether for 180 cycles. As in Example 76, the desired product remained in the extraction solvent, and was recovered as an oil (5.73 g, 65% yield), density 30 C/30 C 1.1680, greater than the monomer mixture (see Examples 15-543 for a description of the composition of the monomer mixture) at 1.0608, and enabling (if in excess) separation by centrifugation for solubility determination and for spectrophotometry. The constancy of the ratios of the characteristic 558 nm peak to the weight % of the dye (14.34, 14.95, and 14.56) proves complete solubility up to 13 wt %, providing A* of at least 1.8 for a 5 micron thickness of the monomer mixture or its corresponding polymer. Solubility of 1-(2-heptylamino)-9,10-anthracenedione to at least 13 wt %, with A* at least 2, was shown similarly. The compound was tested for Absorbance fraction (F) and coloration (A*) as described for Examples 15-43 and the results are reported in Table 7.

Examples 79-88

A number of 1-(alkylamino)-4-hydroxy-9,10-anthracenedione compounds were tested for Absorbance fraction (F) and coloration (A*) as described for Examples 15-43 and the results are reported in Table 7. Table 8 reports the physical properties (melting point, heat of fusion, and glass transition temperature of the 1-(alkylamino)-9,10-anthracenedione compounds of examples 73-88. Mass spectra were consistent with the structures listed in Table 8. Melting points were determined by DSC (10° C./minute) with the temperature of maximal heat flow reported. Heat of fusion was determined by DSC (10° C./minute). Glass transition temperature was determined by DSC (10° C./minute) with the midpoint of the transition temperature reported.

Tables 7 and 8 show data from a preferred class of 9,10-anthracenedione dyes for organic media, including polymers including polytetrafluoroethylene, for example. All of the dyes absorb strongly in the 500-650 nm region, as shown in Table 7 by A*, and relatively much less in the 400 nm region, as shown by F. In each case, except as noted, concentrated dye solutions in a monomer mixture (the composition is described in Examples 15-43) are precisely diluted in ethyl acetate for spectrophotometry. These listed A* values are not upper limits except for the dyes having melting points above 140 C, for which the solutions were proved by centrifugation to be saturated.

The double peak at 555 and 595 nm is characteristic for 1-alkylamino-9,10-anthracenedione, but gives almost no information about the alkyl group. The molar absorbance is the absorbance, in a 1 cm path length, of a 1M solution. The molar absorbance reported in Table 7 is reported for the absorbance of the solution at the 555 nm peak. For the purest dyes of Table 7 it averages approximately 10910+/−180. By using this value a dye sample (e.g., a sample of a monomer mixture or a polymer) can be assayed for maximal molar content of a dye of this class

TABLE 7

Spectrophotometric Data for Nonionic 1-(Alkylamino)-9,10-anthracenedione dyes highly soluble in an exemplary monomer mixture that can be used to make microwell array devices.

| Example | Chemical Abstract Service (CAS) Name | CAS No. | Spectral solvent | Lambda max (nm) | Lambda #2 (nm) | Range, nm 50% max | A* | F | Molar Abs. (555 nm) (×10E4) |
|---|---|---|---|---|---|---|---|---|---|
| 73 | n-Hexyl- | 63768-04-7 | E[a] | 555 | 596 | 505-613 | 0.90 | 0.05 | 1.135 |
| 74 | 3-Methylbutyl- | | E | 556 | 596 | 507-615 | 0.85 | 0.06 | 1.076[c] |
| 76 | 3-Methoxypropyl- | 93982-26-4 | E[b] | 555 | 593 | 502-613 | 0.42 | 0.08 | 1.095[d] |
| 77 | 3-n-Butoxypropyl- | | E | 555 | 595 | 504-615 | 0.73 | 0.05 | ND |
| 78 | 2-Ethylhexyl- | 94023-27-5 | E | 558 | 599 | 505-619 | 1.77 | 0.08 | ND |
| 79 | Decamethylene-(bis) | | E | 555 | 596 | 493-617 | 0.02 | 0.12 | ND |
| 80 | Furfuryl- | | E | 517 | 550 | 450-597 | 0.13 | 0.17 | ND |
| 81 | n-Pentyl- | 63768-03-6 | E | 555 | 596 | 505-614 | 1.22 | 0.07 | ND |
| 82 | Cyclohexyl- | 82206-33-5 | E | 558 | 597 | 510-618 | 0.22 | 0.07 | ND |
| 83 | 2-Heptyl- | | H | 559 | 597 | 508-615 | 1.50 | 0.06 | 1.091 |
| 84 | 3-Ethoxypropyl- | | E | 556 | 596 | 507-615 | 0.88 | 0.04 | ND |

TABLE 7-continued

Spectrophotometric Data for Nonionic 1-(Alkylamino)-9,10-anthracenedione dyes highly soluble in an exemplary monomer mixture that can be used to make microwell array devices.

| Example | Chemical Abstract Service (CAS) Name | CAS No. | Spectral solvent | Lambda max (nm) | Lambda #2 (nm) | Range, nm 50% max | A* | F | Molar Abs. (555 nm) (×10E4) |
|---|---|---|---|---|---|---|---|---|---|
| 85 | 1,1,3,3-Tetramethylbutyl- |  | E | 560 | 601 | 503-620 | 0.62 | 0.62 | ND |
| 86 | 3-Methyl-2-butyl- |  | E | 557 | 599 | 488-616 | 0.70 | 0.15 | ND |
| 87 | 3-Dimethylaminopropyl- | 38866-17-0 | E | 552 | 591 | 502-608 | 0.19 | 0.04 | ND |
| 88 | 1,1-Dimethylethyl- |  | E | 557 | 596 | 364-615 | 0.34 | 0.94 | ND |

[a]A solution of this dye in the monomer mixture gave A* = 2.38, F = 0.14; but the sample, capillary MP 63-70 C., was less pure.
[b]A solution in ethyl acetate gave A* = 1.670, F = 0.05.
[c]Average of 3 measurements; 1.066, 1.078, and 1.093.
[d]Measured on the ethyl acetate solution of note (b).

In Table 8, the melting points of crystalline solids are taken as the temperatures of maximal heat flow at heating rates of 10 C per minute in Differential Scanning calorimetry (DSC), which also provides heats of fusion and (on reheating) glass transition temperatures (Tg). Oils and glasses yield only Tg information. Visual capillary melting points of almost-black dyes are very imprecise, but are closest for purest samples.

All high-resolution mass spectrometry (MS) was performed using an Agilent 6540 Ultra High Definition Q-TOF LC-MS/MS instrument (Agilent Technologies, Inc., Santa Clara, Calif.). The results are reported in Table 8 as calculated (Calc.) values and observed (obs.) formula weight (FW) values.

All thin-layer chromatography (TLC) was performed using Whatman (GE Healthcare Life Sciences Ltd.) MK6F silica gel plates and toluene eluent (unless noted otherwise). Unreacted Quinizarin was detected by its yellow-orange fluorescence using UV or blue illumination. Desired products were observed as purple spots and 1,4-bis(alkylamino) anthraquinone by-products were observed as cyan-blue spots.

TABLE 8

Physical properties of nonionic 1-(Alkylamino)-9,10-anthracenedione dyes that are highly soluble in a monomer mixture used for microwell array articles.

| Example | Chemical Abstrate Service Name | Melting Point (° C.) | H(f) (J/g) | $T_g$ (° C.) | FW (MS) (Calc.) | FW[d] (MS) (Obs.) | FW[e] (Chem.) (Calc.) |
|---|---|---|---|---|---|---|---|
| 73 | n-Hexyl- | 78 | 87.8 | −21 | 323.1513 | 323.1519 | 323.29 |
| 74 | 3-Methylbutyl- | 85 | 84.2 | −20 | 309.1357 | 309.1358 | 309.36 |
| 76 | 3-Methoxypropyl- | 123 | 94.0 | −20 | 311.1149 | 311.1151 | 311.32 |
| 77 | 3-n-Butoxypropyl- | 48 | 44.6 | −34 | 353.1619 | 353.1623 | 353.40 |
| 78 | 2-Ethylhexyl- | Oil | ND | −27 | 351.1826 | 351.1822 | 351.45 |
| 79 | -Decamethylene-(bis)- | 149[a] | 62.5 | −15 | 616.2565 | 616.2568 | 616.70 |
| 80 | Furfuryl- | 174[b] | 74.0 | −14 | 319.0836 | 319.0838 | 319.32 |
| 81 | n-Pentyl- | 81 | 76.0 | −19 | 309.1357 | 309.1361 | 309.36 |
| 82 | Cyclohexyl- | 165 | 90.3 | −13 | 321.1357 | 321.1359 | 321.36 |
| 83 | 2-Heptyl- | Oil | ND | −17 | 337.1670 | 337.1676 | 337.42 |
| 84 | 3-Ethoxypropyl- | 81 | 69.5 | −28 | 325.1306 | 325.1302 | 325.35 |
| 85 | 1,1,3,3-Tetramethylbutyl- | 138[c] | 10.3 | 43 | 351.1826 | 352.1829 | 351.45 |
| 86 | 3-Methyl-2-butyl- | 103 | 80.5 | ND | 309.1357 | 309.1360 | 309.36 |
| 87 | 3-Dimethylaminopropyl- | 68 | 61.2 | 8 | 324.1466 | 324.1471 | 324.38 |
| 88 | 1,1-Dimethylethyl- | 123 | 81.6 | ND | 295.1200 | 295.1200 | 295.35 |

[a]Five trial MPs; 79, 94, 117, 137, and 149 C., observed sequentially.
[b]Two trial MPs; 83 and 174 C., observed sequentially.
[c]Two trial MPs; 83 and 138 C., observed sequentially.
[d]Mass spectral monoisotopic exact Formula Weights (FW).
[e]Chemical Formula Weights; calculated using natural isotopic abundances of the component elements.

Example 89

The following colorants (listed by their respective generic names from the Color Index) were added to the monomer mixture (50 wt % 1,6-hexanediol diacrylate) in the weight percent ratio listed below:

| | |
|---|---|
| Disperse violet 29 | 4.00% |
| Solvent blue 36 | 1.5% |
| Solvent violet 11 | 0.6% |
| Solvent violet 37 | 0.5% |
| Disperse red 11 | 0.6% |
| Disperse red 15 | 0.8% |

Figure 10:
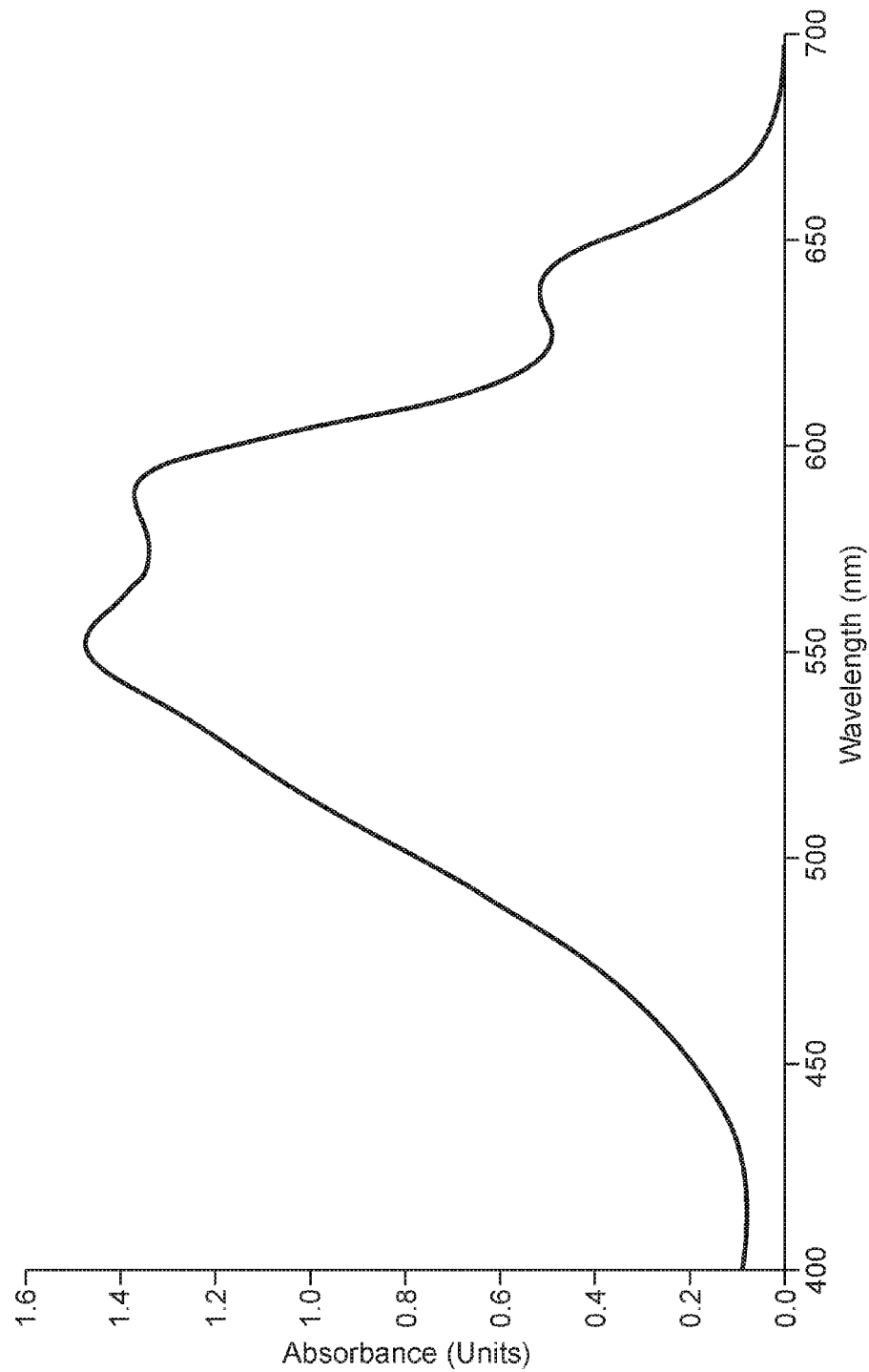
FIG. 10 is a u.v.-visible spectrogram of a mixture of six colorants.

After thorough mixing, the solution was diluted 1:1000 in spectrophotometric grade ethyl acetate and the absorbance was measured in a split-beam scanning spectrophotometer (reference solution was spectrophotometric grade ethyl acetate). The absorbance spectrum of the mixture is shown in FIG. 10. The spectrum shows very low absorbance at 400-450 nm, an absorbance maximum at about 550 nm, and a secondary absorbance maximum (lambda #2) at about 590 nm.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. An article, comprising
a microstructured layer with upper and lower major surfaces, comprising a plurality of optically-isolated microwells extending below the upper major surface; and
an optically-transmissive flexible layer coupled to the lower major surface of the microstructured layer;
wherein each microwell in the microstructured layer comprises an opening, an optically-transmissive bottom wall, and at least one side wall extending between the opening and the bottom wall;
wherein a first thickness (t) is defined by a thickness of the bottom wall plus a thickness of the optically-transmissive flexible layer;
wherein t is about 2 µm to about 55 µm;
wherein a second thickness (T) is defined by a thickness of the microstructured layer plus the thickness of the optical transmissive layer, wherein T is less than or equal to about 156 µm;
wherein the optically-transmissive flexible layer comprises a film comprising polyethylene terephthalate, polyethylene naphthalate, high density polyethylene, low density polyethylene, or linear low density polyethylene;
wherein the optically-transmissive flexible layer further comprises an adhesive.

2. The article of claim 1, wherein the microstructured layer comprises a colorant.

3. The article of claim 2, wherein the colorant is selected from the group consisting of carbon black, fuchsin, carbazole violet, and Foron Brilliant Blue.

4. The article of claim 1, wherein the optically-transmissive flexible layer is transmissive to a selected wavelength of light.

5. The article of claim 4, wherein the bottom wall is substantially transmissive to the selected wavelength of light.

6. The article of claim 4, wherein the at least one sidewall is substantially nontransmissive to the selected wavelength of light.

7. The article of claim 6, wherein the at least one sidewall is at least 50% less transmissive of a selected wavelength of light than the bottom wall.

8. The article of claim 6, wherein a sidewall is at least 90% less transmissive of a selected wavelength of light than the bottom wall.

9. The article of claim 1, wherein the bottom wall and/or the at least one sidewall of a microwell further comprise a coating.

10. The article of claim 9, wherein the bottom wall and/or the at least one side wall of a microwell further comprises a plurality of coatings.

11. The article of claim 9, wherein at least one coating comprises $SiO_2$.

12. The article of claim 9, wherein at least one coating comprises a reflective coating.

13. The article of claim 1, wherein the microstructured layer is a cured polymer derived from a resin.

14. The article of claim 13, wherein the resin is selected from the group consisting of acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof.

15. The article of claim 14, wherein the film comprises a multi-layer film.

16. The article of claim 1, wherein the microstructured layer further comprises a tab region that is substantially free of microwells.

17. The article of claim 16, wherein the tab region comprises a detachable portion.

18. The article of claim 1, further comprising a cover layer coupled to the upper major surface of the microstructured layer.

19. The article of claim 18, wherein the cover layer is removably coupled to the microstructured layer.

20. The article of claim 1, further comprising a cover layer coupled to the optically-transmissive flexible layer on a surface opposite the microstructured layer.

21. The article of claim 20, wherein the cover layer is removably coupled to the optically-transmissive flexible layer.

22. The article of claim 1, further comprising an optical detection system comprising an optical device, wherein the optical device is optically coupled to a substrate.

23. The article of claim 22, wherein the optical device comprises a fiber optic face plate.

24. The article of claim 22, wherein the optical device comprises a CCD image sensor, a CMOS image sensor, or a photomultiplier tube.

25. The article of claim 22, wherein the optical system further comprises a processor.

26. The article of claim 1, wherein at least one microwell further comprises a polynucleotide.

27. The article of claim 26, wherein the polynucleotide is coupled to a particle.

28. The article of claim 1, wherein the optically-transmissive flexible layer is disposed between at least one bottom wall and the adhesive.

29. An assay system, comprising:
an article according to claim 1;
an imaging device optically coupled thereto; and
a processor.

30. The assay system of claim 29, wherein optically coupled comprises adhesively coupling the microwell array article to a solid interface.

* * * * *